United States Patent [19]
Hance et al.

[11] Patent Number: 5,817,459
[45] Date of Patent: Oct. 6, 1998

[54] NUCLEOTIDE SEQUENCES OF ACTINOMYCETALES, OLIGONUCLEOTIDES OF SAID SEQUENCES AND THEIR USE FOR DETECTING THE PRESENCE OF ACTINOMYCETALES

[75] Inventors: Allan Johnson Hance; Bernard Grandchamp-Desraux; Véronique Levy-Frebault; Brigitte Gicquel, all of Paris, France

[73] Assignees: Institut National de la Sante et de la Recherche Mediale-Inserm; Institute Pasteur, both of Paris, France

[21] Appl. No.: 623,729

[22] PCT Filed: Apr. 13, 1990

[86] PCT No.: PCT/FR90/00274

§ 371 Date: Feb. 11, 1991

§ 102(e) Date: Feb. 11, 1991

[87] PCT Pub. No.: WO90/12875

PCT Pub. Date: Nov. 1, 1990

[30] Foreign Application Priority Data

Apr. 17, 1989 [FR] France ................................. 89 05057

[51] Int. Cl.⁶ ............................. C12Q 1/68; C07H 21/04
[52] U.S. Cl. ........................ 435/6; 435/69.3; 435/91.2; 435/172.3; 436/501; 536/23.1; 536/24.1; 536/24.3; 536/24.31; 536/24.32; 536/24.33; 935/9; 935/77; 935/78
[58] Field of Search .................... 435/6, 69.3, 172.3, 435/91, 91.2; 436/501; 536/27, 23.1, 24.1, 24.3–24.33; 935/9, 77, 78, 88

[56] References Cited

U.S. PATENT DOCUMENTS 4,358,535  11/1982  Falkow et al. ............................. 435/5

FOREIGN PATENT DOCUMENTS

| 0200362 | 12/1986 | European Pat. Off. . |
| 0288306 | 10/1988 | European Pat. Off. . |
| WO8800974 | 2/1988 | WIPO . |
| WO8805823 | 8/1988 | WIPO . |
| WO8806591 | 9/1988 | WIPO . |

OTHER PUBLICATIONS

Tubercle, vol. 69, No. 1, Mar. 1988, Longman Group UK Ltd., (Londres, GB), C.C. Pao et al.: "The detection of mycobacterial DNA sequences in uncultured clinical specimens with cloned *Mycobacterium tuberculosis* DNA as probes", pp. 27–36.

Molecular and Cellular Probes, vol. 2, 1988, Academic Press Ltd, R.N. Picken et al.: "DNA probes for mycobacteria. I. Isolation of DNA probes for the identification of *Mycobacterium tuberculosis* complex and for mycobacteria other than *Tuberculosis* (MOTT)" pp. 111–124.

Molecular Microbiology, vol. 3, No. 7, 1989, (New York, US), A.J. Hance et al.: "Detection and identification of mycobacteria by amplification of mycobacterial DNA" pp. 843–849.

Abstracts of the Annual Meeting of the American Society for Microbiology, vol. 89, No. 0, 1989, (US), B.B. Plikaytis et al.: "Rapid, sensitive and specific detection of mycobacteria using gene amplification techniques", Abstract U–43.

*Primary Examiner*—Ardin H. Marschel
*Attorney, Agent, or Firm*—Flehr Hohbach Test Albritton & Herbert LLP; Walter H. Dreger; Jan P. Brunelle

[57] ABSTRACT

The present invention relates to nucleotide sequences of Actinomycetales, in particular of mycobacteria, to oligonucleotides contained within said nucleotide sequences, to their uses as primers for the synthesis of Actinomycetales DNA and as probes for the detection of DNA and/or the transcription products of Actinomycetales, in particular of mycobacteria, to the products of expression of said sequences, to their uses and to antibodies directed towards the said products, to a method for detecting and identifying Actinomycetales and its uses, as well as to immunogenic compositions comprising the said expression products.

52 Claims, 9 Drawing Sheets

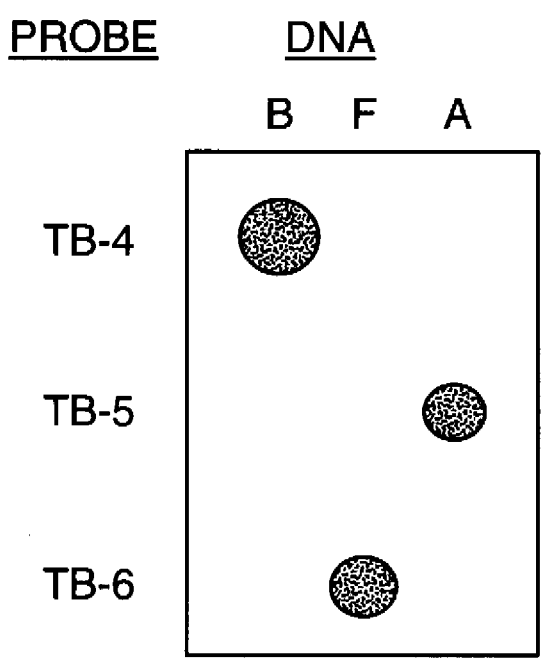
FIG._1

```
                  TYR GLU LYS ILE GLY ALA GLU LEU VAL LYS GLU VAL ALA LYS LYS THR ASP ASP VAL ALA GLY
                G TAC GAG AAG ATC GGC GCC GAG CTG GTC AAA GAG GTA GCC AAG AAG ACC GAT GAC GTC GCC GGT
M. bovis BCG      ASP GLY THR THR THR ALA THR VAL LEU
                  GAC GGC ACC ACG ACG GCC ACC GTG CTG M. avium        - --- --- --- --- --- --- --- --- --- --G --A --C --- --- --- --- --C --- --- --- ---
                  --- --- --G --- --- --- --G --- --C M. para-        - --- --- --- --- --- --- --- --- --- --G --A --C --- --- --- --- --C --- --- --- ---
tuberculosis      --- --- --G --- --- --- --G --- --C M. fortuitum    - --- --- --- --- --- --T --- --C --- --G --A --C --- --- --- --- --C --- --- --G --C
                1 --- --- --- --C --C --- --- --T ---                           50
```

```
M. bovis BCG      ALA GLN ALA LEU VAL ARG GLU GLY LEU ARG ASN VAL ALA ALA GLY ALA ASN PRO LEU GLY LEU
                  GCC CAG GCG TTG GTT CGC GAG GGC CTG CGC AAC GTC GCG GCC GGC GCC AAC CCG CTC GGT CTC
                  LYS ARG GLY ILE GLU LYS ALA VAL GLU
                  AAA CGC GGC ATC GAA AAG GCC GTG GAG M. avium          --- --- --- --- --C --- --- --- --- --- --- --- --- --- --- --- --- --- --G --- ---
                  --G --- --- --- --G --- --- --C ---

M. para-          --- --- --- --- --C --- --- --- --- --- --- --- --- --- --- --- --- --- --G --- ---
tuberculosis      --G --- --- --- --G --- --- --C ---

M. fortuitum      --A --- --C C-- --- --T --A --T --- --- --- --- --T --- --- --- --- --- --- --C --G
                  --G --- --- --- --G --- --- --C ---
                          100                                                          150
```

FIG._2A

```
                LYS VAL THR GLU THR LEU LEU LYS GLY ALA LYS GLU VAL GLU THR LYS GLU GLN ILE ALA ALA
                AAG GTC ACC GAG ACC CTC CTC AAG GGC GCC AAG GAG GTC GAG ACC AAG GAG CAG ATT GCG GCC
M. bovis BCG    THR ALA ALA ILE SER ALA GLY ASP GLN
                ACC GCA GCG ATT TCG GCG GGT GAC CAG
                                                SER                                 ASP
M. avium        --- --- --- --- --- --- --- --- TCG --- --- --- --- --- --- --- --C --- --C --T ---
                --- --G --C --C --C --- --C --- ---
                                                SER                                 ASP
M. para-        --- --- --- --- --- --- --- --- TCG --- --- --- --- --- --- --- --C --- --C --T ---
tuberculosis    --- --G --C --C --C --- --C --- ---
                                                SER
M. fortuitum    --- --- GLY --- --G ---200--G --- A-- --- --- --- --G --- --- --- --- --- --C --T ---
                --- --C -GT --C --C --C --- --- ---
                    250

SER ILE GLY ASP LEU ILE ALA GLU ALA MET ASP LYS VAL GLY ASN GLU GLY VAL ILE THR VAL
                TCC ATC GGT GAC CTG ATC GCC GAG GCG ATG GAC AAG GTG GGC AAC GAG GGC GTC ATC ACC GTC
M. bovis BCG    GLU GLU SER
                GAG GAG TCC
M. avium        --G --- --C --- --- --- --- --- --- --- --- --- --C --- --- --- --- --- --- --- ---
                --- --- ---
M. para-        --G --- --C --- --- --- --- --- --- --- --- --- --C --- --- --- --- --- --- --- ---
tuberculosis    --- --- ---
M. fortuitum    --- --- --- --- --- --- --- --- --C --- --- --- --C --- --- --- --T --- --- --- ---
                --- --- AG-                          300
                        343
```

FIG._2B

```
         10         20         30         40         50         60         70         80         90        100
TACGAGAAGATCGGCGCCGAGCTGGTCAAGGAAGTCGCCAAGAAGACCGACGACGTCGCCGGTGACGGCCACGACGGCCACGGTGCTCGCCCAGGCGT
^         ^    ^    ^                   ^              ^         ^    ^                        ^    ^      ^
MBOII AHAII ALUI                MBOII TTHIIII      HAPII                              EAEI  BSPI286 ECORII
SAU3A                                  AATII       HPHI                               HAEIII HGIAI  SCRFI
      BANI                             AHAII       MAEIII
      HAEIII
      NARI
      CFOI 110        120        130        140        150        160        170        180        190        200
TGGTCCGGCGAGGGCCTGCGCAACGTCGCCGGCCGCCAACCCGCTGGGTCTCAAGCGCATCGAGAAGGCCGTCGAGAAGGTCACCGAGACCCCTGCT
^    ^    ^    ^      ^      ^^ ^^^^^^                   ^^^  ^    ^              ^^^       ^
AFLI MNLI AOSI ACCII AHAII                       CFOI SFANI        HAEIII          BSTEII
SAU96A SAU96A  FNU4HI CFOI                       ACCII TAQI        TAQI            MAEIII
ACCII HAEIII   EAEI BANI                         FNU4HI            HPHI
               XMAIII BSTXI
               CFOI
               HAEIII
               NAEI
               HAPII
               HAEII
               NARI 210        220        230        240        250        260        270        280        290        300
CAAGTCGGCCAAGGAGGTCGAGAGACCAAGGACCAGTCGCTGCCACCGCGATCGACCTCCGCGGGCGACCAGTCGATCGGCGACCTGATCGCCGAGGCGATG
^    ^    ^    ^    ^    ^   ^^^^^ ^^^^^               ^^^^^         ^^                      ^         ^
EAEI  MNLI     STYI      SAU3A BGLI ACCII              SACII         TAQI                    SAU3A    MNLI
HAEIII TAQI              BBVI  SACII                   ACCII         PVUI
STYI                     FNU4HI FNU4HI                               SAU3A
                         AFLI   EAEI
                         SAU96A HAEIII 310        320        330        340
GACAAGGTCGGCAACGAGAGGCGTCATCACCGTCGAGGAGTCC
^        ^        ^    ^     ^
TTHIII   MNLI     HPHI TAQI HINFI
         AHAII         MNLI
         HGAI
```

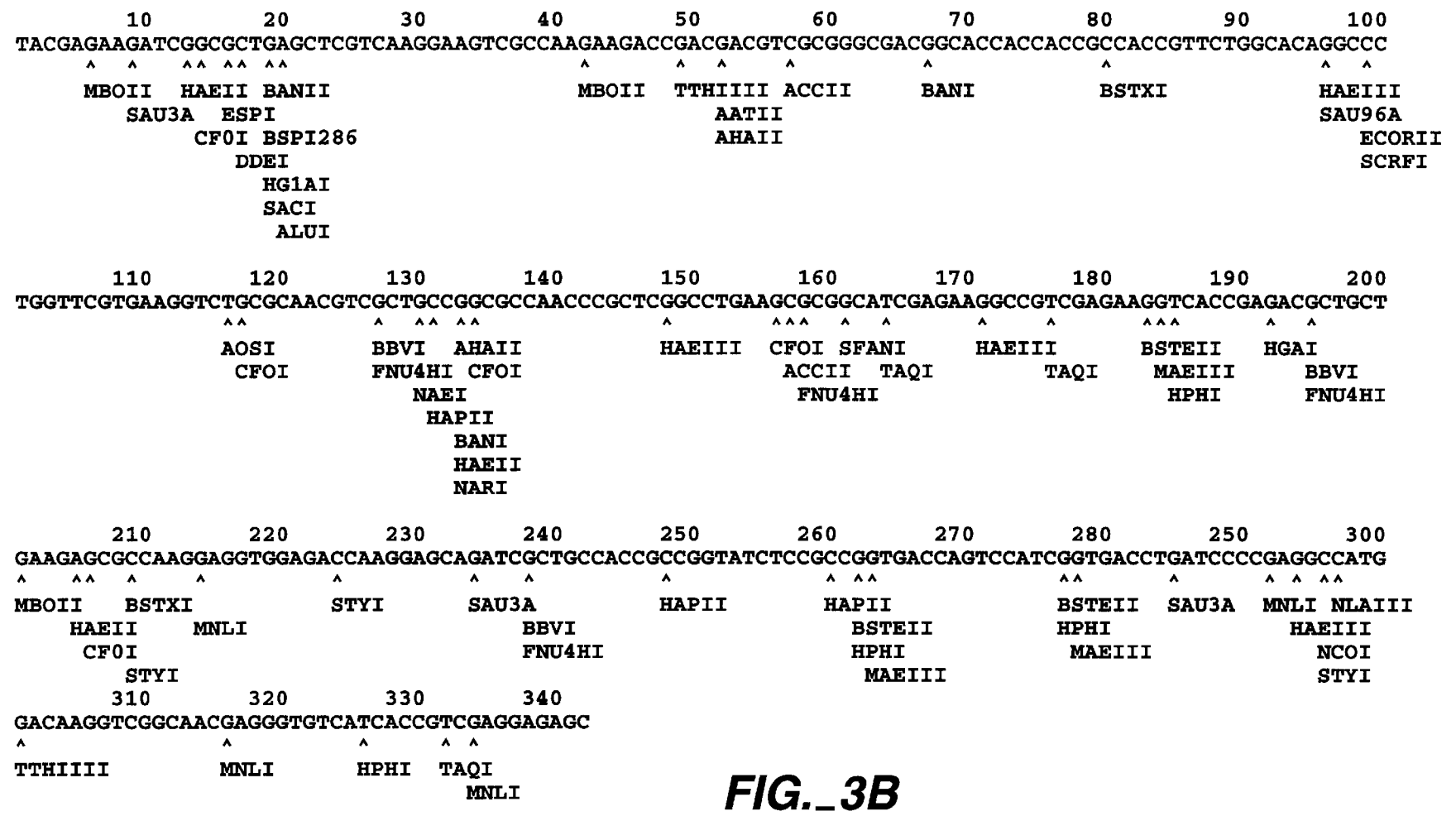

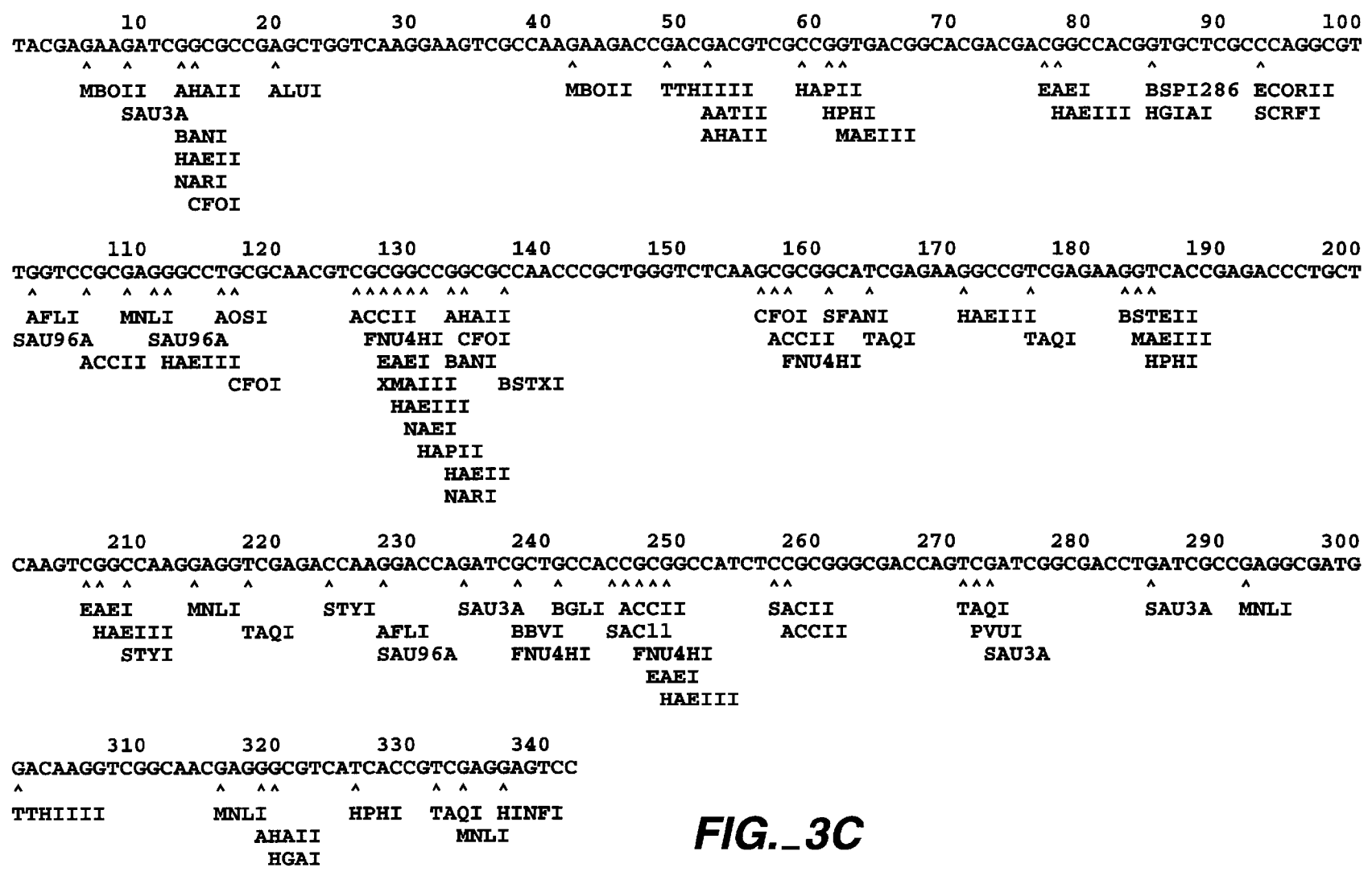

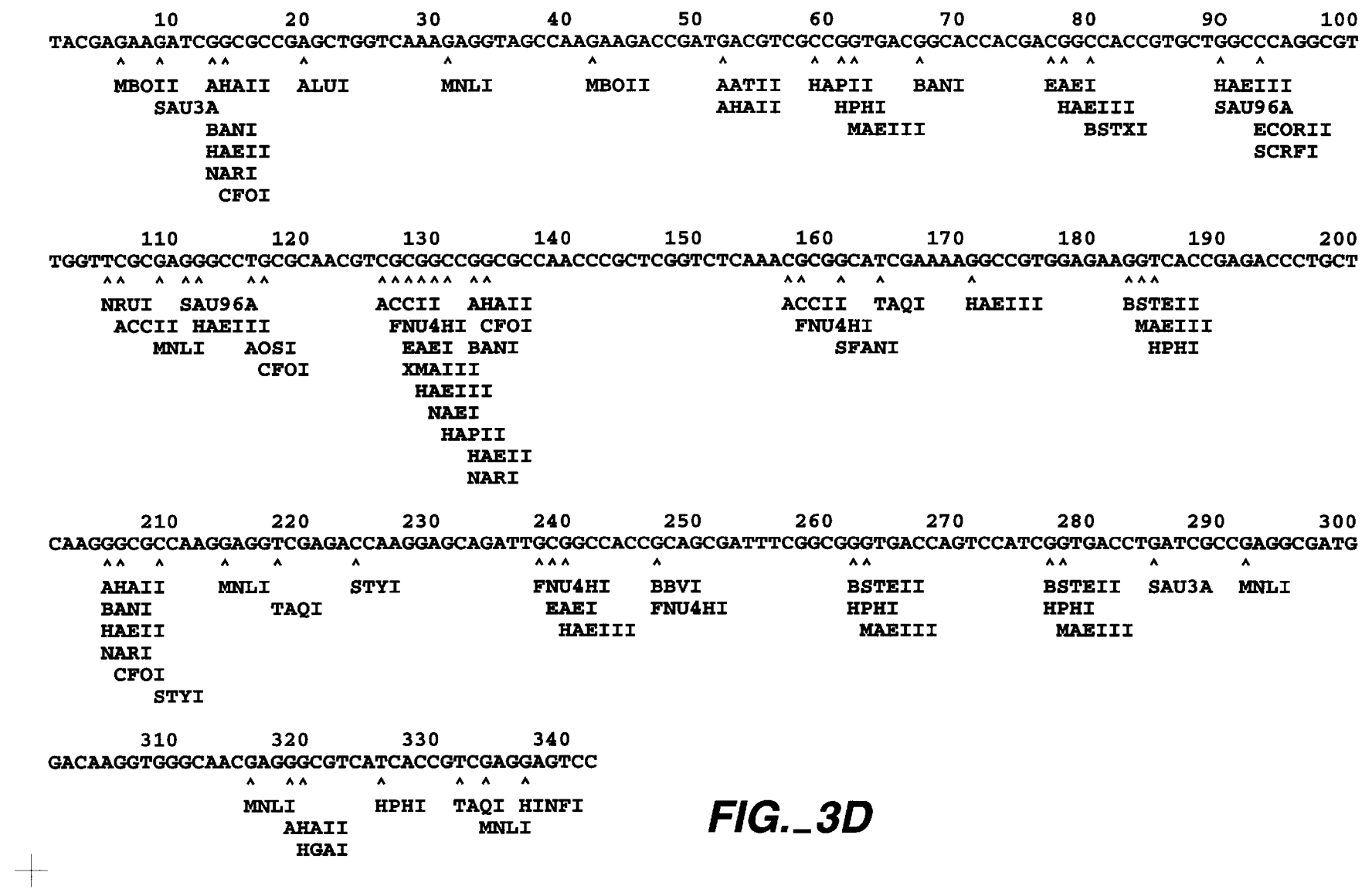

FIG._4A
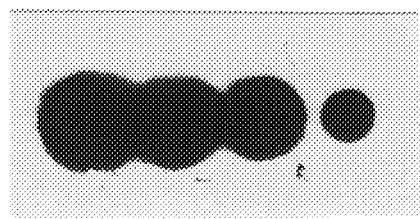
FIG._4B

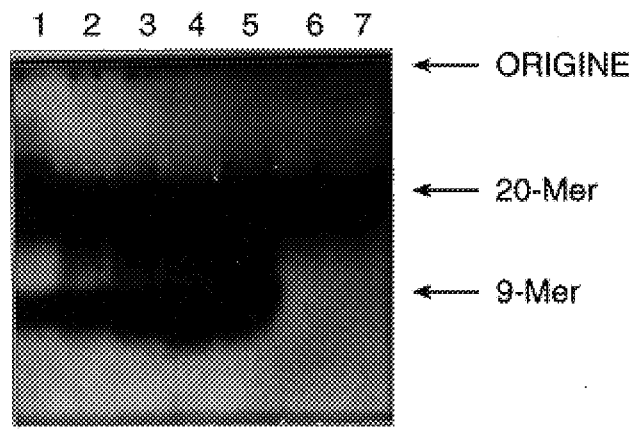
FIG._5
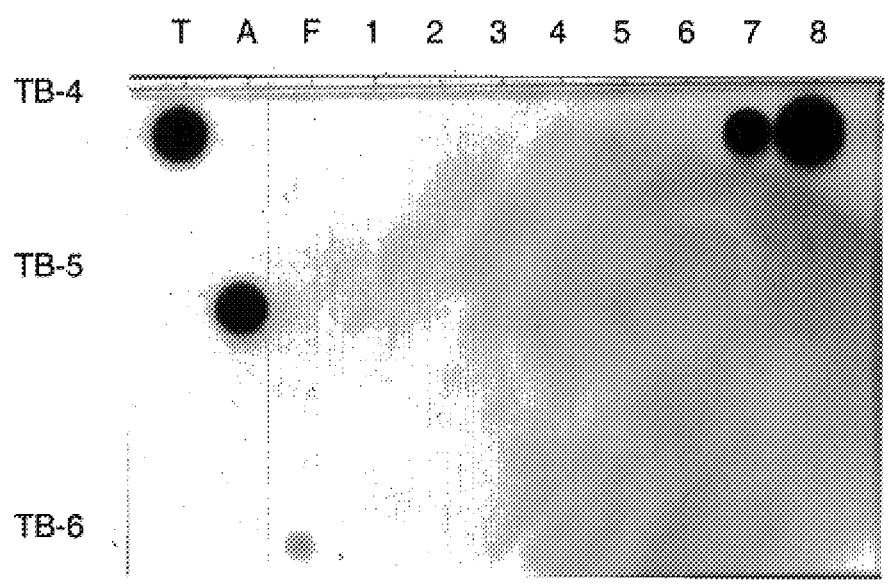
FIG._6

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa Tyr Glu Lys Ile Gly Ala Glu Leu Val Xaa Glu Val Ala Lys Lys
 1               5                  10                  15
Thr Asp Asp Val Ala Xaa Asp Xaa Thr Thr Ala Thr Val Leu Xaa
            20              25                  30
Gln Xaa Leu Val Xaa Glu Gly Leu Arg Asn Val Ala Ala Gly Ala Asn
        35                  40                  45
Xaa Leu Xaa Xaa Lys Xaa Gly Ile Glu Lys Ala Val Glu Xaa Val Thr
 50                  55                  60
Xaa Xaa Leu Leu Xaa Xaa Ala Lys Glu Val Glu Thr Lys Xaa Gln Ile
 65                  70                  75                  80
Ala Ala Thr Ala Xaa Ile Ser Xaa Gly Asp Xaa Ser Ile Gly Xaa Xaa
                 85                  90                  95
Ile Xaa Xaa Xaa Met Asp Lys Val Gly Xaa Glu Gly Val Ile Thr Xaa
            100                 105                 110
Xaa Glu Ser Xaa
            115
```

( 2 ) INFORMATION FOR SEQ ID NO:2:

( i ) SEQUENCE CHARACTERISTICS:
        ( A ) LENGTH: 342 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:2:

```
TACGAGAAGA TCGGCGCTGA GCTCGTCAAG GAAGTCGCCA AGAAGACCGA CGACGTCGCG      60
GGCGACGGCA CCACCACCGC CACCGTTCTG GCACAGGCCC TGGTTCGTGA AGGTCTGCGC     120
AACGTCGCTG CCGGCGCCAA CCCGCTCGGC CTGAAGCGCG GCATCGAGAA GGCCGTCGAG     180
AAGGTCACCG AGACGCTGCT GAAGAGCGCC AAGGAGGTGG AGACCAAGGA GCAGATCGCT     240
GCCACCGCCG GTATCTCCGC CGGTGACCAG TCCATCGGTG ACCTGATCGC CGAGGCCATG     300
GACAAGGTCG GCAACGAGGG TGTCATCACC GTCGAGGAGA GC                        342
```

( 2 ) INFORMATION FOR SEQ ID NO:3:

( i ) SEQUENCE CHARACTERISTICS:
        ( A ) LENGTH: 342 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| TACGAGAAGA | TCGGCGCCGA | GCTGGTCAAG | GAAGTCGCCA | AGAAGACCGA | CGACGTCGCC | 60 |
| GGTGACGGCA | CGACGACGGC | CACGGTGCTC | GCCCAGGCGT | TGGTCCGCGA | GGGCCTGCGC | 120 |
| AACGTCGCGG | CCGGCGCCAA | CCCGCTGGGT | CTCAAGCGCG | GCATCGAGAA | GGCCGTCGAG | 180 |
| AAGGTCACCG | AGACCCTGCT | CAAGTCGGCC | AAGGAGGTCG | AGACCAAGGA | CCAGATCGCT | 240 |
| GCCACCGCGG | CCATCTCCGC | GGGCGACCAG | TCGATCGGCG | ACCTGATCGC | CGAGGCGATG | 300 |
| GACAAGGTCG | GCAACGAGGG | CGTCATCACC | GTCGAGGAGT | CC | | 342 |

( 2 ) INFORMATION FOR SEQ ID NO:4:

( i ) SEQUENCE CHARACTERISTICS:
        ( A ) LENGTH: 342 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| TACGAGAAGA | TCGGCGCCGA | GCTGGTCAAA | GAGGTAGCCA | AGAAGACCGA | TGACGTCGCC | 60 |
| GGTGACGGCA | CCACGACGGC | CACCGTGCTG | GCCCAGGCGT | TGGTTCGCGA | GGGCCTGCGC | 120 |
| AACGTCGCGG | CCGGCGCCAA | CCCGCTCGGT | CTCAAACGCG | GCATCGAAAA | GGCCGTGGAG | 180 |
| AAGGTCACCG | AGACCCTGCT | CAAGGGCGCC | AAGGAGGTCG | AGACCAAGGA | GCAGATTGCG | 240 |
| GCCACCGCAG | CGATTTCGGC | GGGTGACCAG | TCCATCGGTG | ACCTGATCGC | CGAGGCGATG | 300 |
| GACAAGGTGG | GCAACGAGGG | CGTCATCACC | GTCGAGGAGT | CC | | 342 |

( 2 ) INFORMATION FOR SEQ ID NO:5:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
| GTACGAGAAG | ATCGGCGCCG | AGCTGGTCGA | GGAAGTCGCC | AAGAAGACCG | ACGACGTCGC | 60 |
| CGGCGACGGC | ACCACCACGG | CCACTGTGCT | CGCGCAGGCG | TTGGTCAAAG | AGGGCCTGCG | 120 |
| CAACGTCGCG | GCCGGCGCCA | ACCCACTGGG | CCTGAAGCGC | GGCATCGAGA | AGGCAGTCGA | 180 |
| GAAGGTCACC | GAGACGCTGC | TCAAGGGCGC | CAAGGAGGTC | GAGACCAAGG | AGCAGATCGC | 240 |
| TGCCACCGCG | GCCATCTCCG | CCGGTGACCA | GTCGATCGGC | GACCTGATCG | CCGATGGCAT | 300 |
| GGACAAGGTC | GGCAACGAGG | GTGTCATCAC | CGTTGAGGAG | TCC | | 343 |

( 2 ) INFORMATION FOR SEQ ID NO:6:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:6:

| | | | | | | |
|---|---|---|---|---|---|---|
| CTACGAGAAG | ATCGGCGCCG | AGCTGGTCAA | GGAAGTCGCC | AAGAAGACCG | ACGACGTGGC | 60 |
| CGGTGACCGG | ACGACGACGG | CCACCGTGCT | GGTGCAGGCG | CTGGTCAAAG | AGGGCCTGCG | 120 |

```
CAACGTCGCG  GCCGGTGCCA  ACCTGCTCAG  CTTCAAGTGC  GGCATCGAGA  AGGCGGTCGA        180

GAAGGTCACC  GAGACCCTGC  TCAAGCCGGC  CAAGGAGGTC  GAGACCAAGG  AGCAGATCGC        240

CGCGACCGCC  GTGATCTCGG  TGGGCGACCA  GTCGATCGGT  GACCTGATCG  CCGAGGCGAT        300

GGACAAGGTT  GGCAACGAGG  GCGTCATCAC  CGTCGAGGAG  TCC                          343
```

( 2 ) INFORMATION FOR SEQ ID NO:7:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:7:

```
CTACGAGAAG  ATCGGCGCCG  AGCTGGTCAA  AGAGGTCGCC  AAGAAGACCG  ACGATGTCGC         60

CGGTGACCGG  ACCACCACGG  CCACCGTGCT  GGCACAGGCG  CTGGTCAAGG  AAGGCCTGCG        120

CAACGTTGCG  GCCGGTGCCA  ACCCGCTCGG  TCTGAAGCGC  GGCATTGAGA  AGGCAGTCGA        180

GAAGGTCACC  GAGACCTTGC  TCAAGTCGGC  CAAAGAGGTC  GAGACCAAGG  AGCAGATCGC        240

GGCGACCGCA  GCCATCTCCG  CCGGCGACCA  GTCGATCGGC  GACCCGATCG  TCGAGGCGAT        300

GGACAAGGTC  GGCAACGAGG  GCGTCATTAC  CGTCGAGGAG  TCC                          343
```

( 2 ) INFORMATION FOR SEQ ID NO:8:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:8:

```
CTACGAGAAG  ATCGGCGCCG  AGCTGGTCAA  GGAAGTCGCC  AAGAAGACCG  ACGACGTCGC         60

GGCTGACGGC  ACCACCACCG  CCACCGTGCT  CGCCCAGCGG  CTGGTGCGCG  AGGGTCTGCG        120

CAACGTGGCC  GCGGGCGCGA  ACCCGCTGGG  CCTCAAGCGC  GGCATCGAGA  AGGCCGTCGA        180

GGCCGTGACC  GCCAAGCTGC  TCGACACCGC  CAAGGAGGTC  GAGACCAAGG  AGCAGATCGC        240

CGCCACCGCG  GGCATCTCCG  CGGGCGACGC  GTCCATCGGT  GAGCTGATCG  CCGAGGCCAT        300

GGACAAGGTC  GGCAAGGAAG  GCGTCATCAC  CGTCGAGGAG  AGC                          343
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GAGATCGAGC  TGGAGGATCC                                                        20
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:10:

AGCTGCAGCC CAAAGGTGTT 20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGGCATCGA AAAGGCCGTG 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CGAAATCGCT GCGGTGGCCG 20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CTGCCACCGC GGCCATCTCC 20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CTGCCACCGC CGGTATCTCC 20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AACGTCGCGG CCGGCGCCAA                                                                      20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GACTCCTCGA CGGTGATGAC                                                                      20

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CCTGCTCAAG GGCGCCAAG                                                                       19

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CGAAATCGCT GCGGTGGCCG CAATCTGCTC                                                            30

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGTGCTCGCC CAGGCGTTGG TCCGC                                                                 25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TGTGCTCGCG CAGGCGCTGG TCAAA                                                                 25

( 2 ) INFORMATION FOR SEQ ID NO:21:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Tyr Glu Lys Ile Gly Ala Glu Leu Val Lys Glu Val Ala Lys Lys Thr
 1               5                  10                  15
Asp Asp Val Ala Gly Asp Gly Thr Thr Thr Ala Thr Val Leu Ala Gln
                20                  25                  30
Ala Leu Val Arg Glu Gly Leu Arg Asn Val Ala Ala Gly Ala Asn Pro
            35                  40                  45
Leu Gly Leu Lys Arg Gly Ile Glu Lys Ala Val Glu Lys Val Thr Glu
    50                  55                  60
Thr Leu Leu Lys Ser Ala Lys Glu Val Glu Thr Lys Glu Gln Ile Ala
65                  70                  75                  80
Ala Thr Ala Gly Ile Ser Ala Gly Asp Gln Ser Ile Gly Asp Leu Ile
                85                  90                  95
Ala Glu Ala Met Asp Lys Val Gly Asn Glu Gly Val Ile Thr Val Glu
                100                 105                 110
Glu Ser
```

( 2 ) INFORMATION FOR SEQ ID NO:22:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Tyr Glu Lys Ile Gly Ala Glu Leu Val Lys Glu Val Ala Lys Lys Thr
 1               5                  10                  15
Asp Asp Val Ala Gly Asp Gly Thr Thr Thr Ala Thr Val Leu Ala Gln
                20                  25                  30
Ala Leu Val Arg Glu Gly Leu Arg Asn Val Ala Ala Gly Ala Asn Pro
            35                  40                  45
Leu Gly Leu Lys Arg Gly Ile Glu Lys Ala Val Glu Lys Val Thr Glu
    50                  55                  60
Thr Leu Leu Lys Ser Ala Lys Glu Val Glu Thr Lys Asp Gln Ile Ala
65                  70                  75                  80
Ala Thr Ala Ala Ile Ser Ala Gly Asp Gln Ser Ile Gly Asp Leu Ile
                85                  90                  95
Ala Glu Ala Met Asp Lys Val Gly Asn Glu Gly Val Ile Thr Val Glu
                100                 105                 110
Glu Ser
```

( 2 ) INFORMATION FOR SEQ ID NO:23:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO:23:

| Tyr | Glu | Lys | Ile | Gly | Ala | Glu | Leu | Val | Glu | Val | Ala | Lys | Lys | Thr |
|---|---|---|---|---|---|---|---|---|---|---|---|---|---|---|
| 1 | | | | 5 | | | | | 10 | | | | | 15 |

| Asp | Asp | Val | Ala | Gly | Asp | Gly | Thr | Thr | Ala | Thr | Val | Leu | Ala | Gln |
|---|---|---|---|---|---|---|---|---|---|---|---|---|---|---|
| | | | 20 | | | | | 25 | | | | | 30 | |

| Ala | Leu | Val | Lys | Glu | Gly | Leu | Arg | Asn | Val | Ala | Ala | Gly | Ala | Asn | Pro |
|---|---|---|---|---|---|---|---|---|---|---|---|---|---|---|---|
| | | | 35 | | | | | 40 | | | | | 45 | | |

| Leu | Gly | Leu | Lys | Arg | Gly | Ile | Glu | Lys | Ala | Val | Glu | Lys | Val | Thr | Glu |
|---|---|---|---|---|---|---|---|---|---|---|---|---|---|---|---|
| | 50 | | | | | 55 | | | | | 60 | | | | |

| Thr | Leu | Leu | Lys | Gly | Ala | Lys | Glu | Val | Glu | Thr | Lys | Glu | Gln | Ile | Ala |
|---|---|---|---|---|---|---|---|---|---|---|---|---|---|---|---|
| 65 | | | | | 70 | | | | | 75 | | | | | 80 |

| Ala | Thr | Ala | Ala | Ile | Ser | Ala | Gly | Asp | Gln | Ser | Ile | Gly | Asp | Leu | Ile |
|---|---|---|---|---|---|---|---|---|---|---|---|---|---|---|---|
| | | | | 85 | | | | | 90 | | | | | 95 | |

| Ala | Asp | Gly | Met | Asp | Lys | Val | Gly | Asn | Glu | Gly | Val | Ile | Thr | Ser | Gly |
|---|---|---|---|---|---|---|---|---|---|---|---|---|---|---|---|
| | | | 100 | | | | | 105 | | | | | 110 | | |

| Glu | Ser |
|---|---|

(2) INFORMATION FOR SEQ ID NO:24:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

| Tyr | Glu | Lys | Ile | Gly | Ala | Glu | Leu | Val | Lys | Glu | Val | Ala | Lys | Lys | Thr |
|---|---|---|---|---|---|---|---|---|---|---|---|---|---|---|---|
| 1 | | | | 5 | | | | | 10 | | | | | 15 | |

| Asp | Asp | Val | Ala | Gly | Asp | Arg | Thr | Thr | Ala | Thr | Val | Leu | Val | Gln |
|---|---|---|---|---|---|---|---|---|---|---|---|---|---|---|
| | | | 20 | | | | | 25 | | | | | 30 | |

| Ala | Leu | Val | Lys | Glu | Gly | Leu | Arg | Asn | Val | Ala | Ala | Gly | Ala | Asn | Leu |
|---|---|---|---|---|---|---|---|---|---|---|---|---|---|---|---|
| | | | 35 | | | | | 40 | | | | | 45 | | |

| Leu | Ser | Phe | Lys | Cys | Gly | Ile | Glu | Lys | Ala | Val | Glu | Lys | Val | Thr | Glu |
|---|---|---|---|---|---|---|---|---|---|---|---|---|---|---|---|
| | 50 | | | | | 55 | | | | | 60 | | | | |

| Thr | Leu | Leu | Lys | Pro | Ala | Lys | Glu | Val | Glu | Thr | Lys | Glu | Gln | Ile | Ala |
|---|---|---|---|---|---|---|---|---|---|---|---|---|---|---|---|
| 65 | | | | | 70 | | | | | 75 | | | | | 80 |

| Ala | Thr | Ala | Val | Ile | Ser | Val | Gly | Asp | Gln | Ser | Ile | Gly | Asp | Leu | Ile |
|---|---|---|---|---|---|---|---|---|---|---|---|---|---|---|---|
| | | | | 85 | | | | | 90 | | | | | 95 | |

| Ala | Glu | Ala | Met | Asp | Lys | Val | Gly | Asn | Glu | Gly | Val | Ile | Thr | Val | Glu |
|---|---|---|---|---|---|---|---|---|---|---|---|---|---|---|---|
| | | | 100 | | | | | 105 | | | | | 110 | | |

| Glu | Ser |
|---|---|

(2) INFORMATION FOR SEQ ID NO:25:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

| Asp | Pro | Tyr | Glu | Lys | Ile | Gly | Ala | Glu | Leu | Val | Lys | Glu | Val | Ala | Lys |
|---|---|---|---|---|---|---|---|---|---|---|---|---|---|---|---|
| 1 | | | | 5 | | | | | 10 | | | | | 15 | |

| Lys | Thr | Asp | Asp | Val | Ala | Gly | Asp | Arg | Thr | Thr | Thr | Ala | Thr | Val | Leu |
|---|---|---|---|---|---|---|---|---|---|---|---|---|---|---|---|

|  | | | | | | 20 | | | | | 25 | | | | | 30 | |
|---|---|---|---|---|---|---|---|---|---|---|---|---|---|---|---|---|---|

Ala Gln Ala Leu Val Lys Glu Gly Leu Arg Asn Val Ala Gly Ala
     35                          40                    45

Asn Pro Leu Gly Leu Lys Arg Gly Ile Glu Lys Ala Val Glu Lys Val
     50                          55                    60

Thr Glu Thr Leu Leu Lys Ser Ala Lys Glu Val Glu Thr Lys Glu Gln
65                       70                    75                    80

Ile Ala Ala Thr Ala Ala Ile Ser Ala Gly Asp Gln Ser Ile Gly Asp
              85                    90                    95

Pro Ile Val Glu Ala Met Asp Lys Val Gly Asn Glu Gly Val Ile Thr
         100                       105                      110

Val Glu Glu Ser Asn Thr Phe Gly Leu Gln
         115                       120

(2) INFORMATION FOR SEQ ID NO:26:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Tyr Glu Lys Ile Gly Ala Glu Leu Val Lys Glu Val Ala Lys Lys Thr
1                5                    10                      15

Asp Asp Val Ala Ala Asp Gly Thr Thr Thr Ala Thr Val Leu Ala Gln
         20                          25                    30

Arg Leu Val Arg Glu Gly Leu Arg Asn Val Ala Ala Gly Ala Asn Pro
         35                          40                    45

Leu Gly Leu Lys Arg Gly Ile Glu Lys Ala Val Glu Ala Val Thr Ala
     50                          55                    60

Lys Leu Leu Asp Thr Ala Lys Glu Val Glu Thr Lys Glu Gln Ile Ala
65                       70                    75                    80

Ala Thr Ala Gly Ile Ser Ala Gly Asp Ala Ser Ile Gly Glu Leu Ile
              85                    90                    95

Ala Glu Ala Met Asp Lys Val Gly Lys Glu Gly Val Ile Thr Val Glu
         100                       105                      110

Glu Ser (2) INFORMATION FOR SEQ ID NO:27:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Tyr Glu Lys Ile Gly Ala Glu Leu Val Lys Glu Val Ala Lys Lys Thr
1                5                    10                      15

Asp Asp Val Ala Gly Asp Gly Thr Thr Thr Ala Thr Val Leu Ala Gln
         20                          25                    30

Ala Leu Val Arg Glu Gly Leu Arg Asn Val Ala Ala Gly Ala Asn Pro
         35                          40                    45

Leu Gly Leu Lys Arg Gly Ile Glu Lys Ala Val Glu Lys Val Thr Glu
     50                          55                    60

|     | Thr | Leu | Leu | Lys | Gly | Ala | Lys | Glu | Val | Glu | Thr | Lys | Glu | Gln | Ile | Ala |
|-----|-----|-----|-----|-----|-----|-----|-----|-----|-----|-----|-----|-----|-----|-----|-----|-----|
|     | 65  |     |     |     | 70  |     |     |     |     | 75  |     |     |     |     |     | 80  |

|     | Ala | Thr | Ala | Ala | Ile | Ser | Ala | Gly | Asp | Gln | Ser | Ile | Gly | Asp | Leu | Ile |
|-----|-----|-----|-----|-----|-----|-----|-----|-----|-----|-----|-----|-----|-----|-----|-----|-----|
|     |     |     |     |     | 85  |     |     |     | 90  |     |     |     |     |     | 95  |     |

|     | Ala | Glu | Ala | Met | Asp | Lys | Val | Gly | Asn | Glu | Gly | Val | Ile | Thr | Val | Glu |
|-----|-----|-----|-----|-----|-----|-----|-----|-----|-----|-----|-----|-----|-----|-----|-----|-----|
|     |     |     |     | 100 |     |     |     |     | 105 |     |     |     |     | 110 |     |     |

Glu Ser ( 2 ) INFORMATION FOR SEQ ID NO:28:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
TACGAGAAGA  TCGGCGCCGA  GCTGGTCAAG  GAAGTCGCCA  AGAAGACCGA  CGACGTCGCC      60
GGTGACGGCA  CGACGACGGC  CACGGTGCTC  CCCCAGGCGT  TGGTCCGCGA  GGGCCTGCGC     120
AACGTCGCGG  CCGGCGCCAA  CCCGCTGGGT  CTCAAGCGCG  GCATCGAGAA  GGCCGTCGAG     180
AAGGTCACCG  ACACCCTGCT  CAAGTCGGCC  AAGGAGGTCG  AGACCAAGGA  CCAGATCGCT     240
GCCACCGCGG  CCATCTCCGC  GGGCGACCAG  TCGATCGGCG  ACCTGATCGC  CGAGGCGATG     300
GACAAGGTCG  GCAACGAGGG  CGTCATCACC  GTCGAGGAGT  CC                         342
```

( 2 ) INFORMATION FOR SEQ ID NO:29:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
TACGAGAAGA  TCGGCGCTGA  GCTCGTCAAG  GAAGTCGCCA  AGAAGACCGA  CGACGTCGCG      60
GGCGACGGCA  CCACCACCGC  CACCGTTCTG  GCACAGGCCC  TGGTTCGTGA  AGGTCTGCGC     120
AACGTCGCTG  CCGGCGCCAA  CCCGCTCGGC  CTGAAGCGCG  GCATCGAGAA  GCCCGTCGAG     180
AAGGTCACCG  AGACGCTGCT  GAAGAGCGCC  AAGGAGGTGG  AGACCAAGGA  GCAGATCGCT     240
GCCACCGCCG  GTATCTCCGC  CGGTGACCAG  TCCATCGGTG  ACCTGATCCC  CGAGGCCATG     300
GACAAGGTCG  GCAACGAGGG  TGTCATCACC  GTCGAGGAGA  GC                         342
```

( 2 ) INFORMATION FOR SEQ ID NO:30:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
TACGAGAAGA  TCGGCGCCGA  GCTGGTCAAG  GAAGTCGCCA  AGAAGACCGA  CGACGTCGCC      60
GGTGACGGCA  CGACGACGGC  CACGGTCCTC  GCCCAGGCGT  TGGTCCGCGA  GGGCCTGCGC     120
AACGTCGCGG  CCGGCGCCAA  CCCGCTGGGT  CTCAAGCGCG  GCATCGAGAA  GGCCGTCGAG     180
```

```
AAGGTCACCG  AGACCCTGCT  CAAGTCGGCC  AAGGAGGTCG  AGACCAAGGA  CCAGATCGCT      240

GCCACCGCGG  CCATCTCCGC  GGGCGACCAG  TCGATCGGCG  ACCTGATCGC  CGAGGCGATG      300

GACAAGGTCG  GCAACGAGGG  CGTCATCACC  GTCGAGGAGT  CC                          342
```

( 2 ) INFORMATION FOR SEQ ID NO:31:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

```
TACGAGAAGA  TCGGCGCCGA  GCTGGTCAAA  GAGGTAGCCA  AGAAGACCGA  TGACGTCGCC      60

GGTGACGGCA  CCACGACGGC  CACCGTGCTG  GCCCAGGCGT  TGGTTCGCGA  GGGCCTGCGC      120

AACGTCGCGG  CCGGCGCCAA  CCCGCTCGGT  CTCAAACGCG  GCATCGAAAA  GGCCGTGGAG      180

AAGGTCACCG  AGACCCTGCT  CAAGGGCGCC  AAGGAGGTCG  AGACCAAGGA  GCAGATTGCG      240

GCCACCGCAG  CGATTTCGGC  GGGTGACCAG  TCCATCGGTG  ACCTGATCGC  CGAGGCGATG      300

GACAAGGTGG  GCAACGAGGG  CGTCATCACC  GTCGAGGAGT  CC                          342
```

NUCLEOTIDE SEQUENCES OF ACTINOMYCETALES, OLIGONUCLEOTIDES OF SAID SEQUENCES AND THEIR USE FOR DETECTING THE PRESENCE OF ACTINOMYCETALES

The present invention relates to nucleotide sequences of Actinomycetales, in particular of mycobacteria, to oligonucleotides contained within the said sequences, to their uses as primers for the synthesis of Actinomycetales DNA and as probes for the detection of DNA and/or of the transcription products of Actinomycetales, in particular of mycobacteria, to the products of expression of the said sequences, to their uses and to antibodies directed towards the said products, to a method for detecting and identifying Actinomycetales and its uses, as well as to immunogenic compositions comprising the said expression products.

Tuberculosis and leprosy are known to be major public health problems. They are currently approximately $60 \times 10^6$ individuals suffering from tuberculosis in the world (with an annual mortality of $3 \times 10^6$), and approximately $15 \times 10^6$ individuals suffering from leprosy. In France, approximately $10^4$ new cases of tuberculosis appear every year. Vaccination with BCG (Bacillus Calmette-Guérin, an attenuated strain of *M. bovis*) is far from effective in all populations. This efficacy varies approximately from 80% in Western countries such as England to 0% in India (results of the latest vaccination trial in Chingleput). The appearance of strains of *M. tuberculosis* resistant to the usual antituberculosis agents and the existence of mycobacterioses due to other, increasingly common mycobacteria such as *M. avium*, especially in patients with immunosuppression (AIDS in the largest number of cases), add to the urgency of developing a rapid method of detecting and identifying mycobacteria.

The diagnosis of tuberculosis and other related mycobacterioses is difficult to carry out; in effect the microorganisms responsible for these diseases are often present in small amounts, and when the amount of them is detectable by the methods conventionally used, the disease is already progressing and the patients are contagious to those around them. As a result of the very long generation time of these bacteria (24 h for *M. tuberculosis* compared with 20 min for *E. coli*), culturing these organisms is difficult. Thus, it requires 6 to 8 weeks to identify the microorganisms, and longer to obtain an antibiogram usable for appropriate treatment of the patients. The need for a detection test not requiring culturing of the microorganisms, and directly usable with the pathological samples even when the microorganisms are present therein at low concentrations, is hence essential.

Several techniques are currently used in clinical practice for identifying a mycobacterial infection.

In the first place, direct detection of the microorganisms in the microscope should be mentioned; this technique is rapid, but does not permit identification of the mycobacterial species observed, and lacks sensitivity in as much as a large number of microorganisms have to be present in the sample ($>10^4$/ml) in order to permit reliable detection (RATES J., CHEST, 1979, 76, (suppl.), 757–763).

Cultures, when positive, have a specificity approaching 100%, and permit identification of the mycobacterial species isolated; nevertheless, as specified above, growth of mycobacteria in vitro can be achieved only in the space of 3 to 6 weeks, and when few mycobacteria are present at the site of infection, repeated culturing is necessary in order to ensure a positive result (BATES J., 1979 and BATES J. et al., Am. Rev. Respir. Dis., 1986, 134, 415–417).

Serological techniques can prove useful under some conditions, but their use is limited by their low sensitivity and/or their low specificity (DANIEL T. M. et al., Am. Rev. Respir. Dis., 1987, 135, 1137–1151).

The presence or absence of mycobacteria may also be determined by hybridisation with DNA or RNA using probes specific for DNA sequences (KIEHN T. E. et al., J. Clin. Microbiol., 1987, 25, 1551–1552; ROBERTS M. C. et al., J. Clin. Microbiol., 1987, 25, 1239–1243; DRAKE T. A. et al., J. Clin. Microbiol., 1987, 25, 1442–1445). However, these methods also require culturing of the microorganisms.

Some DNA sequences of various mycobacteria, and in particular some genes coding for mycobacterial antigens have been described. There may be mentioned, in particular, PCT International Application WO 88/00,974, whose inventor is YOUNG R. and the content of which is recapitulated in a paper published in Nature, 1985, 316, 450; these publications describe the genes coding for five immunodominant antigens of *M. leprae* and, in particular, the gene coding for the 65-kD antigen has been sequenced. There may also be mentioned PCT International Application WO 88/05,823, whose co-inventors are HUSSON R., YOUNG R. and SHINNICK T. and the content of which is recapitulated in the paper published in J. Bact., 1987, 169, 1080–1088 and which describes the genes of *M. tuberculosis* coding for protein antigens, and in particular for the 65-kD antigen. This International Application specifies, in particular, that the genes of *M. tuberculosis* coding for five immunologically active proteins were isolated by systematic screening of a recombinant DNA library expressed in a bacteriophage lambda gt11, with a collection of monoclonal antibodies directed towards the protein antigens of this bacterium. One of the antigens of *M. tuberculosis*, a 65-kD protein possesses determinants common to *M. tuberculosis* and *M. leprae*.

PCT International Application WO 88/06,591, a co-inventor of which is, in particular, T. SHINNICK, describes a recombinant protein of 540 amino acids (65-kD protein) and also the DNA sequence and the vectors for the expression of the said protein, as well as the uses of the said recombinant protein. This Application also describes peptides corresponding to sequences of this protein and their uses.

Genes coding for proteins of other mycobacteria (*M. africanum, M. smegmatis, M. bovis* BCG and *M. avium*) have also been isolated. There may be mentioned, in particular, THOLE et al. (Infect. Immunol., 1987, 55, 1466–1475), who have described a 64-kD protein of *M. bovis* BCG expressed in *E. coli*.

However, the amounts of mycobacterial DNA present in most biological samples are insufficient to give a positive signal; this technique has hence proved unsuitable for the identification of mycobacterial DNA extracted directly from biological samples.

A number of studies have also shown some degree of structural homology between the different mycobacteria. However, differences in the DNA sequence of *M. tuberculosis* and *M. bovis* have been described in the 3' region of the open reading frame of the 65-kD antigen (SHINNICK et al., 1987, THOLE et al., 1987), but a homologous region has not been observed in the DNA of *M. leprae* (MEHRA et al., Proc. Nat. Acad. Sci. USA, 1986, 83, 7013–7017, also PCT 88/000,974).

There are also publications which describe vaccines against mycobacteria, produced by genetic engineering; there may be mentioned, in particular, PCT International Application WO 88/02,027, which describes recombinant poxviruses capable of expressing mycobacterial antigens and which enable a protective immunological response to mycobacteria to be obtained.

The various detection methods of the prior art do not permit, on the one hand the detection and rapid identification of an Actinomycetales infection directly from a biological sample, and on the other hand the specific identification of groups, species or strains, which may even be present in small amounts.

The additional references which follow also constitute the state of the art prior to the present invention.

BAESS I., Acta Path. Microbiol. Scand., 1979, 87, 221–226; BEAUCAGE S. L. et al., Tetrahedron Lett., 1981, 22, 1859–1862; EISENACH K. D. et al., Am. Rev. Respir. Dis., 1986, 133, 1065–1068; GHEORGHIU M. et al., J. Biol. Standardization, 1988, 16, 15–26; GLASSROTH J. et al., N. Engl. J. Med., 1980, 302, 1441–1450; HAWKINS C. C. et al., Ann. Intern. Med., 1985, 105, 184–188; IMAEDA T., Int. J. Systematic Bacteriol., 1985, 35, 147–150; IMAEDA T. et al., Int. J. Systematic Bacteriol., 1988, 38, 151–156; KOGAN S. C. et al., N. Engl. J. Med., 1987, 317, 985–990; LI H. et al., Nature (Lond.), 1988, 335, 414–417; LU M. C. et al., Infect. Immun., 1987, 55, 2378–2382; MANIATIS T. et al., 1982, Cold Spring Harbor, New York; McFADDEN J. J. et al., Mol. Microbiol., 1987, 1, 283–291; PAO C. C. et al., Tubercle, 1988, 69, 27–36; PATEL R., J. Gen. Microbiol., 1986, 132, 541–551; SAIKI R. K. et al., Science, 1988, 239, 487–491; SANGER F. et al., Proc. Natl. Acad. Sci. USA, 1977, 74, 5463–5467; SMIDA J. et al., Int. J. Leprosy, 1988, 56, 449–454; THEIN S. L. et al., in Human Genetic Diseases, 1986, IRL Press, 33–50; THOLE J. E. R. et al., Infect. Immun., 1985, 50, 800–806; WATSON E. A., Canad. J. Pub. Health, 1935, 26, 268–275; WOLINSKY E., Am. Rev. Respir. Dis, 1979, 119, 107–159.

BRIEF DESCRIPTION OF THE FIGURES

FIG. 1 shows the hybridisation of amplified DNA of $M.$ $bovis$ (B), $M.$ $avium$ (A) and $M.$ $fortuitum$ (F) with the specific probes TB-4 (SEQ ID NO:12), TB-5 (SEQ ID NO:13) and TB-6 (SEQ ID NO:14), respectively.

FIG. 2 shows the DNA sequences of the amplified fragments obtained from the gene coding for the 65 kD antigen of $M.$ $bovis,$ $M.$ $avium,$ $M.$ $paratuberculosis$ and $M.$ $fortuitum.$ FIGS. 3a–3d show a number of restriction sites of the fragments of 343 nucleotides contained within the gene encoding the 65 kD antigen of $M.$ $avium$ (FIG. 3a), $M.$ $fortuitum$ (FIG. 3b), $M.$ $paratuberculosis$ (FIG. 3c) and $M.$ $bovis$ (FIG. 3d).

FIGS. 4a and 4b show a gel and a dot blot, respectively, demonstrating results for the detection assay for DNA extracted from samples containing $10^6$ human mononuclear blood cells and $6\times10^5$ (column 1), $6\times10^4$ (column 2), $6\times10^3$ (column 3), 600 (column 4) 60 (column 5) and 6 (column 6) $M.$ $bovis$ bacilli, and amplified using Taq polymerase and the oligonucleotide primers TB-1 (SEQ ID NO:9) and TB-2 (SEQ ID NO:10).

FIG. 5 shows the detection of amplified mycobacterial DNA sequences by the oligonucleotide restriction test wherein purified mycobacterial DNA is amplified and equivalent amounts of the amplified product from $M.$ $avium$ (columns 1∝5), $M.$ $bovis$ BCG (column 6) and $M.$ $fortuitum$ (column 7) are evaluated.

FIG. 6 shows the results from the analysis of mycobacterial DNA in a sputum specimen wherein DNA purified from $M.$ $tuberculosis$ (T), $M.$ $avium$ (A) and from $M.$ $fortuitum$ (F) and DNA extracted from sputum samples which yielded a negative culture (columns 1–6) or a positive culture for $M.$ $tuberculosis$ (columns 7 and 8) was amplified using Taq polymerase in the case of PCR or using another polymerase and the oligonucleotides TB-1 (SEQ ID NO:9) and TB-2 (SEQ ID NO:10).

The aim of the present invention is accordingly to provide a detection and identification method enabling small amounts of DNA extracted from microorganisms, themselves present in limited numbers, to be detected, the method being rapid and enabling Actinomycetales infection, and in particular a mycobacterial infection, a Nocardia infection or a Rhodococcus infection, to be identified directly in pathological samples without having to carry out culturing.

The subject of the present invention is a nucleotide sequence derived from Actinomycetales, characterised in that it consists of a homologous sequence of a gene common to Actinomycetales chosen from the group comprising mycobacteria, Nocardia and Rhodococcus, within which sequence there are conserved regions and variable regions, and in that it comprises between 250 and 500 base pairs.

Nucleotide sequence is understood, in the present invention, to mean both a double-stranded DNA sequence, a single-stranded DNA sequence and the products of transcription of the said DNA sequences.

Actinomycetales is understood, in the sense used in the present invention, to mean both Actinomycetaceae such as Nocardia and Mycobacteriaceae or Rhodococcus.

There are at least 50 species of mycobacteria divided into several groups. In the present invention, the group comprising $M.$ $bovis$ BCG, $M.$ $bovis,$ $M.$ $tuberculosis,$ $M.$ $africanum$ and $M.$ $microti$ is referred to as the tuberculosis bacillus group; and the group comprising $M.$ $avium,$ $M.$ $intracellulare$ and $M.$ $paratuberculosis$ is referred to as the MAIP group.

Comparison of the nucleotide sequences of the different groups and/or species has enabled identical or similar fragments to be demonstrated within a gene common to the different groups, and a homology to be defined between the different sequences.

According to an advantageous embodiment of the invention, the said sequence possesses an at least 80% homology with the gene coding for the 65-kD mycobacterial antigen.

According to an advantageous variant of this embodiment, the said sequence comprise 383 base pairs homologous in at least 8 species of mycobacteria, namely $M.$ $tuberculosis,$ $M.$ $avium,$ $M.$ $fortuitum,$ $M.$ $paratuberculosis,$ BCG, $M.$ $kansasii,$ $M.$ $malmoense$ and $M.$ $marinum.$ The 383 base pairs correspond to the expression product having an amino acid sequence of the following formula (I): SEQ ID NO:1)

$X_1$—TYR—GLU—LYS—ILE—GLY—ALA—GLU—LEU—VAL—$X_2$—GLU—VAL—ALA—
LYS—LYS—THR—ASP—ASP—VAL—ALA—$X_3$—ASP—$X_4$—THR—THR—THR—ALA—
THR—VAL—LEU—$X_5$—GLN—$X_6$—LEU—VAL—$X_7$—GLU—GLY—LEU—ARG—ASN—VAL—
ALA—ALA—GLY—ALA—ASN—$X_8$—LEU—$X_9$—$X_{10}$—LYS—$X_{11}$—GLY—ILE—GLU—

-continued

LYS—ALA—VAL—GLU—X$_{12}$—VAL—THR—X$_{13}$—X$_{14}$—LEU—LEU—X$_{15}$—X$_{16}$—ALA—
LYS—GLU—VAL—GLU—THR—LYS—X$_{17}$—GLN—ILE—ALA—ALA—THR—ALA—X$_{18}$—
ILE—SER—X$_{19}$—GLY—ASP—X$_{20}$—SER—ILE—GLY—X$_{21}$—X$_{22}$—ILE—X$_{23}$—X$_{24}$—
X$_{25}$—MET—ASP—LYS—VAL—GLY—X$_{26}$—GLU—GLY—VAL—ILE—THR—X$_{27}$—X$_{28}$—
GLU—SER—X$_{29}$ in which:
$X_1$ is non-existent or represents the sequence ASP-PRO,
$X_2$ represents LYS or GLU,
$X_3$ represents GLY or ALA,
$X_4$ represents GLY or ARG,
$X_5$ represents ALA or VAL,
$X_6$ represents ALA or ARG,
$X_7$ represents ARG or LYS,
$X_8$ represents PRO or LEU,
$X_9$ represents GLY or SER,
$X_{10}$ represents LEU or PHE,
$X_{11}$ represents ARG or CYS,
$X_{12}$ represents LYS or ALA,
$X_{13}$ represents GLU or ALA,
$X_{14}$ represents THR or LYS,
$X_{15}$ represents LYS or ASP,
$X_{16}$ represents SER, GLY, PRO or THR
$X_{17}$ represents ASP or GLU,
$X_{18}$ represents ALA, GLY or VAL,
$X_{19}$ represents ALA or VAL,
$X_{20}$ represents GLN or ALA,
$X_{21}$ represents ASP or GLU,
$X_{22}$ represents LEU or PRO,
$X_{23}$ represents ALA or VAL,
$X_{24}$ represents GLU or ASP,
$X_{25}$ represents ALA or GLY,
$X_{26}$ represents ASN or LYS,
$X_{27}$ represents VAL or SER,
$X_{28}$ represents GLU or GLY,
$X_{29}$ is non-existent or represents the sequence ASN-THR-PHE-GLY-LEU-GLN.

According to another advantageous variant of this embodiment, the said sequence comprises 343 base pairs and corresponds to the formula (II) (SEQ ID NO:2) below:

```
   1          11          21          31          41          51          61   (II)
G  TACGAGAAGA  TCGGCGCTGA  GCTCGTCAAG  GAAGTCGCCA  AGAAGACCGA  CGACGTCGCG
   ATGCTCTTCT  AGCCGCGACT  CGAGCAGTTC  CTTCAGCGGT  TCTTCTGGCT  GCTGCAGCGC 71          81          91         101         111         121
GGCGACGGCA  CCACCACCGC  CACCGTTCTG  GCACAGGCCC  TGGTTCGTGA  AGGTCTGCGC
CCGCTGCCGT  GGTGGTGGCG  GTGGCAAGAC  CGTGTCCGGG  ACCAAGCACT  TCCAGACGCG 131         141         151         161         171         181
AACGTCGCTG  CCGGCGCCAA  CCCGCTCGGC  CTGAAGCGCG  GCATCGAGAA  GGCCGTCGAG
TTGCAGCGAC  GGCCGCGGTT  GGGCGAGCCG  GACTTCGCGC  CGTAGCTCTT  CCGGCAGCTC 191         201         211         221         231         241
AAGGTCACCG  AGACGCTGCT  GAAGAGCGCC  AAGGAGGTGG  AGACCAAGGA  GCAGATCGCT
TTCCAGTGGC  TCTGCGACGA  CTTCTCGCGG  TTCCTCCACC  TCTGGTTCCT  CGTCTAGCGA 251         261         271         281         291         301
GCCACCGCCG  GTATCTCCGC  CGGTGACCAG  TCCATCGGTG  ACCTGATCGC  CGAGGCCATG
CGGTGGCGGC  CATAGAGGCG  GCCACTGGTC  AGGTAGCCAC  TGGACTAGCG  GCTCCGGTAC 311         321         331         341
GACAAGGTCG  GCAACGAGGG  TGTCATCACC  GTCGAGGAGA  GC
CTGTTCCAGC  CGTTGCTCCC  ACAGTAGTGG  CAGCTCCTCT  CG
``` and corresponds to a fragment of *M. fortuitum*, similar to the sequence of the mycobacterial gene coding for the 65-kD antigen.

The said fragment comprises, in particular, the following restriction sites:

AccII, AhaII, BanI, BanII, BbvI, Bsp1286, BstXI, CfoI, DdeI, EcoRII, EspI, Fnu4HI, HaeII, HaeIII, HapII, HgaI, HinfI, HphI, MaeIII, MboII, MnlI, NarI, NcoI, NlaIII, SacI, SacII, Sau3A, Sau96A, ScrFI, StyI, TaqI, YmaIII.

According to another advantageous variant of this embodiment, the said sequence comprises 343 base pairs and corresponds to the formula (III)(SEQ ID NO:3) below:

```
                1         11         21         31         41         51         61    (III)
              G TACGAGAAGA TCGGCGCCGA GCTGGTCAAG GAAGTCGCCA AGAAGACCGA CGACGTCGCC
                ATGCTCTTCT AGCCGCGGCT CGACCAGTTC CTTCAGCGGT TCTTCTGGCT GCTGCAGCGG 71         81         91        101        111        112
                GGTGACGGCA CGACGACGGC CACGGTGCTC GCCCAGGCGT TGGTCCGCGA GGGCCTGCGC
                CCACTGCCGT GCTGCTGCCG GTGCCACGAG CGGGTCCGCA ACCAGGCGCT CCCGGACGCG 131        141        151        161        171        181
                AACGTCGCGG CCGGCGCCAA CCCGCTGGGT CTCAAGCGCG GCATCGAGAA GGCCGTCGAG
                TTGCAGCGCC GGCCGCGGTT GGGCGACCCA GAGTTCGCGC CGTAGCTCTT CCGGCAGCTC 191        201        211        221        231        241
                AAGGTCACCG AGACCCTGCT CAAGTCGGCC AAGGAGGTCG AGACCAAGGA CCAGATCGCT
                TTCCAGTGGC TCTGGGACGA GTTCAGCCGG TTCCTCCAGC TCTGGTTCCT GGTCTAGCGA 251        261        271        281        291        301
                GCCACCGCGG CCATCTCCGC GGGCGACCAG TCGATCGGCG ACCTGATCGC CGAGGCGATG
                CGGTGGCGCC GGTAGAGGCG CCCGCTGGTC AGCTAGCCGC TGGACTAGCG GCTCCGCTAC 311        321        331        341
                GACAAGGTCG GCAACGAGGG CGTCATCACC GTCGAGGAGT CC
                CTGTTCCAGC CGTTGCTCCC GCAGTAGTGG CAGCTCCTCA GG
``` and corresponds to a fragment common to the MAIP group similar to the sequence of the mycobacterial gene coding for the 65-kD antigen.

The said fragment comprises, in particular, the 5 following restriction sites:

AccII, AflI, AhaII, BanI, BbvI, BglI, Bsp1286, BstEII, BstXI, CfoI, EaeI, HaeII, HaeIII, HphI, MaeIII, MnlI, NarI, PvuI, SacII, Sau3A, Sau96A, TaqI.

According to another advantageous variant of this embodiment, the said sequence comprises 343 nucleotides and corresponds to the formula (IV) (SEQ ID NO:4) below:

```
                1         11         21         31         41         51         61    (IV)
              G TACGACAAGA TCGGCGCCGA GCTGGTCAAA GAGGTAGCCA AGAAGACCGA TGACGTCGCC
                ATGCTCTTCT AGCCGCGGCT CGACCAGTTT CTCCATCGGT TCTTCTGGCT ACTGCAGCGG 71         81         91        101        111        121
                GGTGACGGCA CCACGACGGC CACCGTGCTG GCCCAGGCGT TGGTTCGCGA GGGCCTGCGC
                CCACTGCCGT GGTGCTGCCG GTGGCACGAC CGGGTCCGCA ACCAAGCGCT CCCGGACGCG 131        141        151        161        171        181
                AACGTCGCGG CCGGCGCCAA CCCGCTCGGT CTCAAACGCG GCATCGAAAA GGCCGTGGAG
                TTGCAGCGCC GGCCGCGGTT GGGCGAGCCA GAGTTTGCGC CGTAGCTTTT CCGGCACCTC 191        201        211        221        231        241
                AAGGTCACCG AGACCCTGCT CAAGGGCGCC AAGGAGGTCG AGACCAAGGA GCAGATTGCG
                TTCCAGTGGC TCTGGGACGA GTTCCCGCGG TTCCTCCAGC TCTGGTTCCT CGTCTAACGC 251        261        271        281        291        301
                GCCACCGCAG CGATTTCGGC GGGTGACCAG TCCATCGGTG ACCTGATCGC CGAGGCGATG
                CGGTGGCGTC GCTAAAGCCG CCCACTGGTC AGGTAGCCAC TGGACTAGCG GCTCCGCTAC 311        321        331        341
                GACAAGGTGG GCAACGAGGG CGTCATCACC GTCGAGGAGT CC
                CTGTTCCACC CGTTGCTCCC GCAGTAGTGG CAGCTCCTCA GG
``` and corresponds to a fragment of the sequence of the gene coding for the. 65-kD antigen of the tuberculosis bacillus group.

The said fragment comprises, in particular, the following restriction sites:

AccII, AhaII, BanI, BbvI, BstXI, CfoI, EaeI, HaeIII, HphI, MaeIII, MnlI, NarI, NrvI, SacII, Sau3A, Sau96A, TaqI.

According to yet another advantageous variant of this embodiment, the said sequence comprises 343 nucleotides and corresponds to the formula (V) (SEQ ID NO: 5) below:

```
                              10         20         30         40         50         60
                       GTACGAGAAG ATCGGCGCCG AGCTGGTCGA GGAAGTCGCC AAGAAGACCG ACGACGTCGC
                       CATGCTCTTC TAGCCGCGGC TCGACCAGCT CCTTCAGCGG TTCTTCTGGC TGCTGCAGCG

.......... .......... .......... .......... .......... ..........
```

-continued

```
            70         80         90        100        110        120
      CGGCGACGGC ACCACCACGG CCACTGTGCT CGCGCAGGCG TTGGTCAAAG AGGGCCTGCG
      GCCGCTGCCG TGGTGGTGCC GGTGACACGA GCGCGTCCGC AACCAGTTTC TCCCGGACGC 130        140        150        160        170        180
      CAACGTCGCG GCCGGCGCCA ACCCACTGGG CCTGAAGCGC GGCATCGAGA AGGCAGTCGA
      GTTGCAGCGC CGGCCGCGGT TGGGTGACCC GGACTTCGCG CCGTAGCTCT TCCGTCAGCT 190        200        210        220        230        240
      GAAGGTCACC GAGACGCTGC TCAAGGGCGC CAAGGAGGTC GAGACCAAGG AGCAGATCGC
      CTTCCAGTGG CTCTGCGACG AGTTCCCGCG GTTCCTCCAG CTCTGGTTCC TGCTCTAGCG 250        260        270        280        290        300
      TGCCACCGCG GCCATCTCCG CCGGTGACCA GTCGATCGGC GACCTGATCG CCGATGGCAT
      ACGGTGGCGC CGGTAGAGGC GGCCACTGGT CAGCTAGCCG CTGGACTAGC GGCTACCGTA 310        320        330        340       343
      GGACAAGGTC GGCAACGAGG GTGTCATCAC CGTTGAGGAG TCC
      CCTGTTCCAG CCGTTGCTCC CACAGTAGTG GCAACTCCTC AGG
``` and corresponds to a fragment of *Mycobacterium kansasii* similar to the sequence of the mycobacterial gene coding for the 65-kD antigen.

The said fragment comprises, in particular, the following restriction sites:

AccII, AhaII, AluI, AosI, BanI, BglI, Bsp1286, BstEII, CfoI, EaeI, HapII, HgaI, HphI, MboII, MhlI, NaeI, NlaIII, RsaI, Sau3A, Sau96A, SfaNI, StyI, TaqI, Tth111I.

According to another advantageous variant of this embodiment, the said sequence comprises 343 nucleotides and corresponds to the formula (VI) (SEQ ID NO:6) below:

```
            10         20         30         40         50         60
      CTACGAGAAG ATCGGCGCCG AGCTGGTCAA GGAAGTCGCC AAGAAGACCG ACGACGTGGC
      GATGCTCTTC TAGCCGCGGC TCGACCAGTT CCTTCAGCGG TTCTTCTGGC TGCTGCACCG 70         80         90        100        110        120
      CGGTGACCGG ACGACGACGG CCACCGTGCT GGTGCAGGCG CTGGTCAAAG AGGGCCTGCG
      GCCACTGGCC TGCTGCTGCC GGTGGCACGA CCACGTCCGC GACCAGTTTC TCCCGGACGC 130        140        150        160        170        180
      CAACGTCGCG GCCGGTGCCA ACCTGCTCAG CTTCAAGTGC GGCATCGAGA AGGCGGTCGA
      GTTGCAGCGC CGGCCACGGT TGGACGAGTC GAAGTTCACG CCGTAGCTCT TCCGCCAGCT 190        200        210        220        230        240
      GAAGGTCACC GACACCCTGC TCAAGCCGGC CAAGGAGGTC GAGACCAAGG AGCAGATCGC
      CTTCCAGTGG CTCTGGGACG AGTTCGGCCG GTTCCTCCAG CTCTGGTTCC TCGTCTAGCG 250        260        270        280        290        300
      CGCGACCGCC GTGATCTCGG TGGGCGACCA GTCGATCGGT GACCTGATCG CCGAGGCGAT
      GCGCTGGCGG CACTAGAGCC ACCCGCTGGT CAGCTAGCCA CTGGACTAGC GGCTCCGCTA 310        320        330        340       343
      GGACAAGGTT GGCAACGAGG GCGTCATCAC CGTCGAGGAG TCC
      CCTGTTCCAA CCGTTGCTCC CGCAGTAGTG GCAGCTCCTC AGG
``` and corresponds to a fragment of *Mycobacterium malmoense* similar to the sequence of the mycobacterial gene coding for the 65-KD antigen.

The said fragment comprises, in particular, the following restriction sites:

AccII, AhaII, AluI, AosI, BanI, BstEII, EaeI EspI, Fnu4HI, HaeII, HinfI, HphI, MboII, MnlI, NaeI, Sau3A, StyI, TaqI, According to yet another advantageous variant of this embodiment, the said sequence comprises 343 nucleotides and corresponds to the formula (VII) (SEQ ID NO:7) below:

```
              10         20         30         40         50         60
      CTACGAGAAG ATCGGCGCCG AGCTGGTCAA AGAGGTCGCC AAGAAGACCG ACGATGTCGC
      GATGCTCTTC TAGCCGCGGC TCGACCAGTT TCTCCAGCGG TTCTTCTGGC TGCTACAGCG 70         80         90        100        110        120
      CGGTGACCGG ACCACCACGG CCACCGTGCT GGCACAGGCG CTGGTCAAGG AAGGCCTGCG
      GCCACTGGCC TGGTGGTGCC GGTGGCACGA CCGTGTCCGC GACCAGTTCC TTCCGGACGC 130        140        150        160        170        180
      CAACGTTGCG GCCGGTGCCA ACCCGCTCGG TCTGAAGCGC GGCATTGAGA AGGCAGTCGA
      GTTGCAACGC CGGCCACGGT TGGGCGAGCC AGACTTCGCG CCGTAACTCT TCCGTCAGCT 190        200        210        220        230        240
      GAAGGTCACC GAGACCTTGC TCAAGTCGGC CAAAGAGGTC GAGACCAAGG AGCAGATCGC
      CTTCCAGTGG CTCTGGAACG AGTTCAGCCG GTTTCTCCAG CTCTGGTTCC TCGTCTAGCG 250        260        270        280        290        300
      GGCGACCGCA GCCATCTCCG CCGGCGACCA GTCGATCGGC GACCCGATCG TCGAGGCGAT
      CCGCTGGCGT CGGTAGAGGC GGCCGCTGGT CAGCTAGCCG CTGGGCTAGC AGCTCCGCTA 310        320        330        340        343
      GGACAAGGTC GGCAACGAGG GCGTCATTAC CGTCGAGGAG TCC
      CCTGTTCCAG CCGTTGCTCC CGCAGTAATG GCAGCTCCTC AGG
``` and corresponds to a fragment of *Mycobacterium marinum*, similar to the sequence of the mycobacterial gene coding for the 65-kD antigen.

The said fragment comprises, in particular, the following restriction sites:

AatI, AosI, AhaII, AluI, BbvI, BstEII, CfoI, EaeI, Fnu4HI, HaeII, HapII, HinfI, MboII, MnlI, NaeI, PvuI, Sau3A, StyI, TaqI, Tth111I.

According to another advantageous variant of this embodiment, the said sequence comprises 343 nucleotides and corresponds to the formula (VIII) (SEQ ID NO: 8) below:

```
              10         20         30         40         50         60
      CTACGAGAAG ATCGGCGCCG AGCTGGTCAA GGAAGTCGCC AAGAAGACCG ACGACGTCGC
      GATGCTCTTC TAGCCGCGGC TCGACCAGTT CCTTCAGCGG TTCTTCTGGC TGCTGCAGCG 70         80         90        100        110        120
      GGCTGACGGC ACCACCACCG CCACCGTGCT CGCCCAGCGG CTGGTGCGCG AGGGTCTGCG
      CCGACTGCCG TGGTGGTGGC GGTGGCACGA GCGGGTCGCC GACCACGCGC TCCCAGACGC 130        140        150        160        170        180
      CAACGTGGCC GCGGGCGCGA ACCCGCTGGG CCTCAAGCGC GGCATCGAGA AGGCCGTCGA
      GTTGCACCGG CGCCCGCGCT TGGGCGACCC GGAGTTCGCG CCGTAGCTCT TCCGGCAGCT 190        200        210        220        230        240
      GGCCGTGACC GCCAAGCTGC TCGACACCGC CAAGGAGGTC GAGACCAAGG AGCAGATCGC
      CCGGCACTGG CGGTTCGACG AGCTGTGGCG GTTCCTCCAG CTCTGGTTCC TCGTCTAGCG
```

-continued

```
          250          260          270          280          290          300
     CGCCACCGCG   GGGATCTCCG   CGGGCGACGC   GTCCATCGGT   GAGCTGATCG   CCGAGGCCAT
     GCGGTGGCGC   CCGTAGAGGC   GCCCGCTGCG   CAGGTAGCCA   CTCGACTAGC   GGCTCCGGTA 310          320          330          340          343
     GGACAAGGTC   GGCAAGGAAG   GCGTCATCAC   CGTCGAGGAG   AGC
     CCTGTTCCAG   CCGTTCCTTC   CGCAGTAGTG   GCAGCTCCTC   TCG

``` and corresponds to a fragment of Nocardia asteroides, similar to the sequence of the mycobacterial gene coding for the 65-kD antigen.

The said fragment comprises, in particular, the following restriction sites:

AccII, AhaII, AluI, AosI, BanI, Bsp1286, CfoI, EaeI, Fnu4HI, HaeIII, HgaI, HphI, MaeIII, MboII, MnlI, NlaIII, SacII, Sau3A, Sau96A, SfaNI, StyI, TaqI, Tth111I.

The subject of the present invention is also oligonucleotides, characterised in that they consist of a fragment of a nucleotide sequence according to the invention.

Among these fragment, special mention may be made of the following:

an oligonucleotides, characterised in that it possesses the following sequence of formula (IX) (SEQ ID NO:9):

5'GAGATCGAGCTGGAGGATCC     (IX).

Such a sequence corresponds, in particular, to the base sequence 397–416 after the start codon of the "+" strand of the gene coding for the 65-kD antigen of the tuberculosis bacillus group; this sequence is hereinafter designated TB-b 1;

an oligonucleotide, characterised in that it possesses the following sequence of formula (X) (SEQ ID NO:10):

5'AGCTGCAGCCCAAAGGTGTT     (X).

Such a sequence is complementary to the base sequence 535–554 after the start codon of the "+" strand of the gene coding for the 65-kD antigen of the tuberculosis bacillus group; this sequence is hereinafter designated TB-2;

an oligonucleotide, characterised in that it possesses the following sequence of formula (XI) (SEQ ID NO:11):

5'GCGGCATCGAAAAGGCCGTG     (XI)

which sequence permits recognition of tuberculosis bacilli and is hereinafter designated TB-3;

an oligonucleotide, characterised in that it possesses the following sequence of formula (XII) (SEQ ID NO:12):

5'CGAAATCGCTGCGGTGGCCG     (XII)

which sequence permits recognition of tuberculosis bacilli and is hereinafter designated TB-4;

an oligonucleotide, characterised in that it possesses the following sequence of formula (XIII) (SEQ ID NO:13):

5'CTGCCACCGCGGCCATCTCC     (XIII)

which sequence permits recognition of MAIP group bacilli and is hereinafter designated TB-5; this oligonucleotide advantageously comprises a single BglI restriction site;

an oligonucleotide, characterised in that it possesses the following sequence of formula (XIV) (SEQ ID NO:14):

5'CTGCCACCGCCGGTATCTCC     (XIV)

which sequence permits recognition of M. fortuitum and is hereinafter designated TB-6;

an oligonucleotide, characterised in that it possesses the following sequence of formula (XV) (SEQ ID NO:15):

5'AACGTCGCGGCCGGCGCCAA 3'     (XV)

which sequence is hereinafter designated TB-7;

an oligonucleotide, characterised in that it possesses the following sequence of formula (XVI) (SEQ ID NO:16);

5'GACTCCTCGACGGTGATGAC 3'     (XVI)

which sequence is hereinafter designated TB-8;

an oligonucleotide, characterised in that it possesses the following sequence of formula (XVII) (SEQ ID NO:17):

5'CCTGCTCAAGGGCGCCAAG 3'     (XVII)

which sequence is hereinafter designated TB-9; this oligonucleotide TB-9 advantageously comprises a single BanI restriction site.

an oligonucleotide, characterised in that it possesses the following sequence of formula (XVIII) (SEQ ID NO:18):

3'CGAAATCGCTGCGGTGGCCGCAATCTGCTC 5'     (XVIII), which sequence permits recognition of tuberculosis group bacilli and is hereinafter designated TB-10.

an oligonucleotide, characterised in that it possesses the following sequence of formula (XIX) (SEQ ID NO:19):

5'GGTGCTCGCCCAGGCGTTGGTCCGC 3'     (XIX)

which sequence permits recognition of MAIP group bacilli and is hereinafter designated TB-11.

an oligonucleotide, characterised in that it possesses the following sequence of formula (XX) (SEQ ID NO:20):

5'TGTGCTCGCGCAGGCGCTGGTCAAA 3'     (XX), which sequence permits specific recognition of M. kansasii and is hereinafter designated TB-12.

According to yet another embodiment, the said oligonucleotides are obtained synthetically using, in particular, an apparatus marketed by APPLIED BIOSYSTEMS (USA).

The subject of the present invention is also pairs of primers for the synthesis of an Actinomycetales DNA or RNA, characterised in that each primer comprises a nucleotide sequence or a fragment of a nucleotide sequence as defined above.

Such primers permit the synthesis of a DNA or RNA sequence or a fragment of the latter present in a gene coding for an antigen present in all Actinomycetales, and in particular the gene coding for the 65-kD antigen.

According to an embodiment of the said pairs of primers, they advantageously consist of an oligonucleotide of formula (IX) (SEQ ID NO:9) (TB-1) paired with an oligonucleotide of formula (X) (SEQ ID NO:10) (TB-2).

According to another embodiment of the said pairs of primers, they advantageously consist of an oligonucleotide of the formula (XV) (SEQ ID NO:15) (TB-7) paired with an oligonucleotide of formula (XV) (SEQ ID NO:16) (TB-8).

The primers TB-1 (SEQ ID NO:9) and TB-2 (SEQ ID NO:10) permit the synthesis of a DNA or RNA sequence present in mycobacteria or related bacteria such as Nocardia or Rhodococcus.

The subject of the present invention is also nucleotide probes, characterised in that they comprise a nucleotide sequence or a fragment of the latter as defined above, where appropriate labelled using a label such as a radioactive isotope, a suitable enzyme, a fluorochrome, an antibody or a base analogue such as that described in French Patent No. 81/24,131.

According to an advantageous embodiment of this invention, the said probe is chosen from the group comprising the oligonucleotides of formulae XI (SEQ ID NO:11) (TB-3), XII (SEQ ID NO:12) (TB-4), XIII (SEQ ID NO:13) (TB-5), XIV (SEQ ID NO:14) (TB-6), XVII (SEQ ID NO:17) (TB-9), XVIII (SEQ ID NO:18) (TB-10), XIX (SEQ ID NO:19) (TB-11) and XX (SEQ ID NO:20) (TB-12).

The probe TB-6 (SEQ ID NO:14) enables *M. fortuitum* to be detected in particular; the probes TB-5 (SEQ ID NO:13) and TB-11 (SEQ ID NO:19) enable MAIP group mycobacteria to be detected; the probes TB-3 (SEQ ID NO:11), TB-4 (SEQ ID NO:12) TB-9 (SEQ ID NO:17) and TB-10 (SEQ ID NO:18) enable mycobacteria of the tuberculosis bacillus group to be detected; and the probe TB-12 enables *M. kansasii* to be detected.

The subject of the present invention is also the peptides or peptide fragments encoded by any one of the sequences defined above. The following may be mentioned in particular:

a peptide and/or peptide fragment, characterised in that it is encoded by the sequence of 343 nucleotides of formula (II) above and corresponds to the formula (XXI) (SEQ ID NO:21) below:

(XXI)
TYR—GLU—LYS—ILE—GLY—ALA—GLU—LEU—
VAL—LYS—GLU—VAL—ALA—LYS—LYS—THR—
ASP—ASP—VAL—ALA—GLY—ASP—GLY—THR—
THR—THR—ALA—THR—VAL—LEU—ALA—GLN—
ALA—LEU—VAL—ARG—GLU—GLY—LEU—ARG—
ASN—VAL—ALA—ALA—GLY—ALA—ASN—PRO—
LEU—GLY—LEU—LYS—ARG—GLY—ILE—GLU—
LYS—ALA—VAL—GLU—LYS—VAL—THR—GLU—
THR—LEU—LEU—LYS—SER—ALA—LYS—GLU—
VAL—GLU—THR—LYS—GLU—GLN—ILE—ALA—
ALA—THR—ALA—GLY—ILE—SER—ALA—GLY—
ASP—GLN—SER—ILE—GLY—ASP—LEU—ILE—ALA—
GLU—ALA—MET—ASP—LYS—VAL—GLY—ASN—
GLU—GLY—VAL—ILE—THR—VAL—GLU—GLU—SER.

a peptide and/or peptide fragment, characterised in that it is encoded by the sequence of 343 nucleotides of formula (III) above and corresponds to the formula (XXII) (SEQ ID NO:22) below:

(XXII)
TYR—GLU—LYS—ILE—GLY—ALA—GLU—LEU—
VAL—LYS—GLU—VAL—ALA—LYS—LYS—THR—
ASP—ASP—VAL—ALA—GLY—ASP—GLY—THR—
THR—THR—ALA—THR—VAL—LEU—ALA—GLN—
ALA—LEU—VAL—ARG—GLU—GLY—LEU—ARG—
ASN—VAL—ALA—ALA—GLY—ALA—ASN—PRO—
LEU—GLY—LEU—LYS—ARG—GLY—ILE—GLU—
LYS—ALA—VAL—GLU—LYS—VAL—THR—GLU—
THR—LEU—LEU—LYS—SER—ALA—LYS—GLU—
VAL—GLU—THR—LYS—ASP—GLN—ILE—ALA—
ALA—THR—ALA—ALA—ILE—SER—ALA—GLY—
ASP—GLN—SER—ILE—GLY—ASP—LEU—ILE—ALA—
GLU—ALA—MET—ASP—LYS—VAL—GLY—ASN—
GLU—GLY—VAL—ILE—THR—VAL—GLU—GLU—SER.

a peptide and/or peptide fragment, characterised in that it is encoded by the sequence of 343 nucleotides of formula (V) and corresponds to the formula (XXIII) (SEQ ID NO:23) below:

(XXIII)
TYR—GLU—LYS—ILE—GLY—ALA—GLU—LEU—
VAL—GLU—GLU—VAL—ALA—LYS—LYS—THR—
ASP—ASP—VAL—ALA—GLY—ASP—GLY—THR—
THR—THR—ALA—THR—VAL—LEU—ALA—GLN—
ALA—LEU—VAL—LYS—GLU—GLY—LEU—ARG—
ASN—VAL—ALA—ALA—GLY—ALA—ASN—PRO—
LEU—GLY—LEU—LYS—ARG—GLY—ILE—GLU—
LYS—ALA—VAL—GLU—LYS—VAL—THR—GLU—
THR—LEU—LEU—LYS—GLY—ALA—LYS—GLU—
VAL—GLU—THR—LYS—GLU—GLN—ILE—ALA—
ALA—THR—ALA—ALA—ILE—SER—ALA—GLY—
ASP—GLN—SER—ILE—GLY—ASP—LEU—ILE—ALA—
ASP—GLY—MET—ASP—LYS—VAL—GLY—ASN—
GLU—GLY—VAL—ILE—THR—SER—GLY—GLU—SER.

a peptide and/or peptide fragment, characterised in that it is encoded by the sequence of 343 nucleotides of formula (VI) and corresponds to the formula (XXIV) (SEQ ID NO:24) below:

(XXIV)

TYR—GLU—LYS—ILE—GLY—ALA—GLU—LEU—
VAL—LYS—GLU—VAL—ALA—LYS—LYS—THR—
ASP—ASP—VAL—ALA—GLY—ASP—ARG—THR—
THR—THR—ALA—THR—VAL—LEU—VAL—GLN—
ALA—LEU—VAL—LYS—GLU—GLY—LEU—ARG—
ASN—VAL—ALA—ALA—GLY—ALA—ASN—LEU—
LEU—SER—PHE—LYS—CYS—GLY—ILE—GLU—LYS—
ALA—VAL—GLU—LYS—VAL—THR—GLU—THR—
LEU—LEU—LYS—PRO—ALA—LYS—GLU—VAL—
GLU—THR—LYS—GLU—GLN—ILE—ALA—ALA—
THR—ALA—VAL—ILE—SER—VAL—GLY—ASP—
GLN—SER—ILE—GLY—ASP—LEU—ILE—ALA—GLU—
ALA—MET—ASP—LYS—VAL—GLY—ASN—GLU—
GLY—VAL—ILE—THR—VAL—GLU—GLU—SER.

a peptide and/or peptide fragment, characterised in that it is encoded by the sequence of 343 nucleotides of formula (VII) and corresponds to the formula (XXV) (SEQ ID NO:25) below:

(XXV)

ASP—PRO—TYR—GLU—LYS—ILE—GLY—ALA—
GLU—LEU—VAL—LYS—GLU—VAL—ALA—LYS—
LYS—THR—ASP—ASP—VAL—ALA—GLY—ASP—
ARG—THR—THR—THR—ALA—THR—VAL—LEU—
ALA—GLN—ALA—LEU—VAL—LYS—GLU—GLY—
LEU—ARG—ASN—VAL—ALA—ALA—GLY—ALA—
ASN—PRO—LEU—GLY—LEU—LYS—ARG—GLY—
ILE—GLU—LYS—ALA—VAL—GLU—LYS—VAL—
THR—GLU—THR—LEU—LEU—LYS—SER—ALA—
LYS—GLU—VAL—GLU—THR—LYS—GLU—GLN—
ILE—ALA—ALA—THR—ALA—ALA—ILE—SER—
ALA—GLY—ASP—GLN—SER—ILE—GLY—ASP—
PRO—ILE—VAL—GLU—ALA—MET—ASP—LYS—
VAL—GLY—ASN—GLU—GLY—VAL—ILE—THR—
VAL—GLU—GLU—SER—ASN—THR—PHE—GLY—
LEU—GLN.

a peptide and/or peptide fragment, characterised in that it is encoded by the sequence of 343 nucleotides of formula (VIII) and corresponds to the formula (XXVI) (SEQ ID NO:26) below:

(XXVI)

TYR—GLU—LYS—ILE—GLY—ALA—GLU—LEU—
VAL—LYS—GLU—VAL—ALA—LYS—LYS—THR—

-continued

ASP—ASP—VAL—ALA—ASP—GLY—THR—THR—
THR—ALA—THR—VAL—LEU—ALA—GLN—ARG—
LEU—VAL—ARG—GLU—GLY—LEU—ARG—ASN—
VAL—ALA—ALA—GLY—ALA—ASN—PRO—LEU—
GLY—LEU—LYS—ARG—GLY—ILE—GLU—LYS—
ALA—VAL—GLU—ALA—VAL—THR—ALA—LYS—
LEU—LEU—ASP—THR—ALA—LYS—GLU—VAL—
GLU—THR—LYS—GLU—GLN—ILE—ALA—ALA—
THR—ALA—GLY—ILE—SER—ALA—GLY—ASP—
ALA—SER—ILE—GLY—GLU—LEU—ILE—ALA—
GLU—ALA—MET—ASP—LYS—VAL—ILE—THR—
VAL—GLU—GLU—SER.

The subject of the present invention is also a composition having immunogenic capability, characterised in that it comprises at least one peptide and/or peptide fragment as defined above, optionally combined with at least one pharmaceutically acceptable vehicle.

The subject of the present invention is also polyclonal or monoclonal antibodies, characterised in that they are obtained by immunisation of a suitable animal with a peptide or peptide fragment according to the invention.

Such antibodies can, in particular, find application for demonstrating the presence of mycobacteria in a suitable sample obtained from a patient to be tested, according to a known method of the ELISA or RIA type.

The subject of the present invention is also a method for the detection and rapid identification, by amplification and hybridisation, of small amounts of Actinomycetales chosen from the group comprising mycobacteria, Nocardia and Rhodococcus, possibly present in a biological sample suitably treated to extract the DNA and/or the transcription products of the said Actinomycetales, which method is characterised in that the said sample:

(1) is brought into contact with a pair of primers according to the invention, to amplify at least one fragment of the said DNA or RNA, (2) after which the amplified DNA or RNA sequence is detected by at least one nucleotide probe according to the invention.

The method carried out in (1) is, in particular, one of the techniques of genetic amplification such as the so-called Q β replicase method (LIZARDI P. M. et al., Biotechnol., 1988, 6) or the so-called PCR (polymerase chain reaction) method described in European Patent Applications No. 200,363, No. 201,184 and No. 229,701 filed by CETUS CO.

Such a method has the advantage of enabling a specific, direct and rapid test distinguishing the different groups of Actinomycetales, and in particular of mycobacteria, to be carried out, on the one hand using non-specific primers which amplify a DNA or RNA fragment, and on the other hand using group- or genus-specific probes.

According to an advantageous embodiment of the said method, it comprises in addition:

(3) cleavage of any probe which has hybridised during the above step (2), using a suitable restriction enzyme;

(4) detection of any probe fragment obtained.

According to a variant of this embodiment, the restriction enzyme is advantageously chosen from the group comprising BanI and BglI.

Such an embodiment has the advantage of enabling a genus or a group of Actinomycetales to be detected.

According to another advantageous embodiment of the said method, the detection of the amplified DNA or RNA sequence is carried out using two suitable nucleotide probes, the said method comprising in addition:

(3) enzymatic coupling of the two hybridised probes;

(4) detection of any fragment obtained containing the two combined probes.

According to another advantageous embodiment of the said method, the DNA is isolated from the biological sample during a step prior to the detection and identification steps, by suspending the centrifugation pellet from the said biological sample in a suitable lysis solution, followed by an incubation at approximately 95° C. for a suitable time, the incubation itself being followed by the addition of a buffer solution to the medium, after which the DNA is extracted by suitable means of extraction.

According to an advantageous variant of this embodiment, the lysis solution employed is a solution comprising 0.1N NaOH, 2M NaCl and 0.5% SDS.

According to another advantageous variant of this embodiment, the incubation is carried out at a temperature of approximately 95° C. for approximately 15 minutes.

The subject of the present invention is, in addition, a ready-to-use kit, outfit or coordinated set for carrying put the method for detecting at least one Actinomycetales bacterium, in particular at least one mycobacterium, characterised in that it comprises, apart from the appropriate amounts of suitable buffers and reagents for carrying out the said detection:

suitable doses of a pair of primers according to the invention;

suitable doses of at least one nucleotide probe or probe fragment according to the invention.

Apart from the foregoing variants, the invention comprises yet other variants which will become apparent from the description which follows, which relates to examples of implementation of the method which is the subject of the present invention.

It should, however, be clearly understood that these examples are given only by way of illustration of the subject of the invention and in no way constitute a limitation of the latter.

Example 1

Detection and comparative identification of *M. tuberculosis*, *M. bovis*, *M. avium* and *M. fortuitum*.

a) Isolation of mycobacterial DNA.

The biological extracts are treated in a suitable manner and then centrifuged. To extract the DNA, the centrifugation pellet is resuspended in 50 µl of 0.1N NaOH containing 2M NaCl and 0.5% SDS and incubated at 95° C. for 15 min (occasional gentle shaking), and then, after the addition of 0.4 ml of 0.1M Tris-HCl, pH 7, the DNA is extracted by three treatments with a phenol/chloroform mixture, precipitated with ethanol and dissolved in 50 µl of 10 mM Tris-HCl, pH 8, containing 0.1 mM EDTA.

b) DNA amplification.

Amplification is carried out as described in SAIKI et al. (Science, 1988, vol. 239, 487–491) and also in European Patent Application No. 200,362: 0.1 ml of a reaction mixture containing 50 mM KCl, 10 mM Tris-HCl (pH 8.3), 1.5–2.4 mM $MgCl_2$, 100 µg/ml of gelatin, 300 µM deoxyribonucleotides (mixture of the 4 deoxyribonucleotides dA, dG, dC and dI), 50 pM of the primers according to the invention designated TB-1 and TB-2, two units of Taq polymerase and 10–50 µl of an extract of a mixture of human cells and mycobacteria or 50 ng of DNA extracted from mycobacteria is maintained at 94° C. (1.5 min), 50° C. (2 min) and 72° C. (2 min) for approximately 40 cycles. After the last cycle, the samples are maintained at 37° C. for 10 min and then stored at 4° C.

c. Analysis of the amplified samples by Southern blot analysis.

10 µl aliquots are removed from the amplified samples and subjected to electrophoresis on 2% agarose gel. The DNA is then transferred onto nylon filters (standard technique: REED K. L. et al., Nucleic Acid Research, 1985, 13, 7207). The filters with DNA are then washed in 2×SSPE solution (20×SSPE solution corresponds to 3.0M NaCl, 200 mM $NaH_2PO_4$ and 20 mM EDTA), then treated with a prehybridisation mixture at 63° C. in a solution comprising 5×SSPE and 5×Denhardt (1×Denhardt solution corresponds to 0.02% of Ficoll, 0.02% of polyvinylpyrrolidone and 0.02% of bovine serum albumin) for 2 hours and then hybridised in the same solution containing three probes according to the invention, TB-4, TB-5 and TB-6, labelled at their 5' end with $^{32}P$ ($2\times10^5$ cpm/ml, specific activity 1–3 µCi/pmol) overnight at 63° C. The blots or deposits obtained are washed for 2 hours at room temperature in 0.1×SSC solution (1×SSC corresponds to 0.15M NaCl and 0.015M Na citrate) containing 0.5% SDS for 2 to 4 minutes at 67°–72° C. in 5×SSPE solution containing 0.5% SDS and 2 hours at room temperature in 0.1×SSC containing 0.5% SDS. The deposits obtained are dried and any hybrids present are visualised by exposure to an XAR-5 film.

In dot-blot analysis, 10 µl of aliquots of amplified samples are denatured by heating to 95° C. for 2 min in 0.2 ml of 0.4M NaOH containing 25 mM EDTA. The samples are cooled rapidly and loaded into the wells of a manifold (BIORAD, (USA)) or minifold (CERA LABO (France)) fitted with a nylon membrane. Each well is washed twice with 0.4 ml of 20×SSPE, the membrane is heated to 80° C. for one hour and hybridisation is carried out as described above. The results as seen in FIG. 1 are obtained.

FIG. 1 shows the hybridisation of amplified DNA of *M. bovis* (B), *M. avium* (A) and *M. fortuitum* (F) with the specific probes TB-4 (SEQ ID NO:12), TB-5 (SEQ ID NO:13) and TB-6 (SEQ ID NO:14), respectively.

Example 2

Comparison of sequences obtained in Example 1 with the DNA sequences as described in the literature.

a) Sequencing of the amplified mycobacterial sequences obtained.

The DNA is extracted with phenol, precipitated with ethanol and redissolved in 10 mM Tris-HCl (pH 8) containing 1 mM EDTA.

The DNA is then digested with the restriction endonucleases PstI and BamHI, cloned into the phages M13mp18 and M13mp19 and sequenced according to SANGER's method using T7 polymerase or Taq polymerase in the presence of d-azaGTP in place of dGTP.

The amplified DNA corresponds to the expected region of the gene coding for the 65-kD mycobacterial antigen, as shown in FIG. 2 (SEQ ID NO:27), in which the DNA sequences of the amplified fragments obtained from the gene coding for the 65-kD antigen of *M. bovis, M. avium, M. paratuberculosis* and *M. fortuitum* are specified.

The sequence of the amplified DNA of *M. bovis* is identical to the corresponding region of the sequence coding for the 65-kD antigen of *M. bovis* (THOLE et al. 1987) and *M. tuberculosis* (SHINNICK et al. 1987).

The sequences of the amplified DNA from *M. avium, M. paratuberculosis* and *M. fortuitum* are very similar to those of *M. bovis* and *M. tuberculosis*, and the deduced translation products corresponding to these sequences are also very similar to the 65-kD antigen of *M. bovis/M. tuberculosis* as shown in FIG. 2 (SEQ ID NO:27).

FIG. 3 shows a number of restriction sites of the fragments of 343 nucleotides contained within the gene coding for the 65-kD antigen of *M. avium* (FIG. 3a) (SEQ ID NO:28), *M. fortuitum* (FIG. 3b) (SEQ ID NO:29), *M. paratuberculosis* (FIG. 3c) (SEQ ID NO:30) and *M. bovis* BCG (FIG. 3d) (SEQ ID NO:31).

Example 3

Development of the sensitivity of the method.

The sensitivity of the method was tested using BCG diluted in a biological medium, pleural fluid. It was possible to detect approximately 10 bacilli per ml of fluid; this represents a considerable improvement on the direct examination tests, which require $10^3$ to $10^4$ bacilli/ml for the detection of mycobacteria, and without identification.

Furthermore, this test may be accomplished much more rapidly than the detection and identification of mycobacteria after enrichment and culturing.

FIG. 4 shows the results obtained for the DNA extracted from samples containing $10^6$ human mononuclear blood cells and $6 \times 10^5$ (column 1), $6 \times 10^4$ (column 2), $6 \times 10^3$ (column 3), 600 (column 4), 60 (column 5) and 6 (column 6) *M. bovis* bacilli, and amplified using Taq polymerase and the oligonucleotide primers TB-1 (SEQ ID NO:9) and TB-2 (SEQ ID NO:10) (FIG. 4a: gel; FIG. 4b: dot blot).

Example 4

Detection of amplified sequences of the tuberculosis bacillus group by the oligonucleotide restriction test.

To detect the presence of amplified sequences of mycobacteria belonging to the tuberculosis bacillus group by the restriction test, $4 \times 10^4$ cpm of oligonucleotide TB-9 (SEQ ID NO:17) labelled with $^{32}$P at its 5' end is mixed with 2 μl of a 10×buffer (40 mM Tris-HCl pH 7.0, 60 mM MgCl$_2$ and 60 mM 2-mercaptoethanol) in a final volume of 15 μl. 4 μl of amplified product are added and the tube is incubated at 95° C. for 5 minutes, transferred to ice and then incubated at 52° C. for 2 hours. 1 μl of BanI (25 units) is added and the tubes are incubated at 37° C. for 1–2 hours. 4 μl of 95% formamide containing 20% of Ficoll, 25 mM EDTA, 25 μg/ml of bromophenol blue and 25 μg/ml of xylene cyanol are added, the tubes are heated to 65° C. for 10 minutes and 12 μl are subjected to electrophoresis on a 30% polyacrylamide gel (340 V for 1–2 hours). The gel is then exposed to an X-ray film for 3–18 hours and the positive samples are identified by the presence of a band corresponding to the fragment of 11 nucleotides at the 5' end of the oligonucleotide TB-9, produced by the cleavage of TB-9 by the restriction enzyme.

Example 5

Synthesis of the oligonucleotides according to the invention.

The oligonucleotides are synthesised using the phosphoramidite method (BEAUCAGE, 1985, loc.cit.) with a 380 D DNA synthesiser (APPLIED BIOSYSTEMS, CA). TB-1 (SEQ ID NO:9), TB-2 (SEQ ID NO:10), TB-3 (SEQ ID NO:11), TB-4 (SEQ ID NO:12), TB-5 (SEQ ID NO:13 ), TB-6 (SEQ ID NO:14 ), TB-7 (SEQ ID NO:15), TB-8 (SEQ ID NO:16 ), and TB-9 (SEQ ID NO:17) are thereby obtained.

Example 6

Detection of amplified sequences of MAIP group by the oligonucleotide restriction test.

The protocol is identical to that of Example 4; however, a number of reagents are different:

the oligonucleotide TB-5 (SEQ ID NO:13), is used;

the 1× buffer contains 500 mM Tris-HCl pH 8.0, 100 mM MgCl$_2$ and 400 mM NaCl;

the restriction enzyme used is BglI (10 units).

As in Example 4, the positive samples are identified by the presence of a band corresponding to a fragment of 9 nucleotides resulting from cleavage of the oligonucleotide TB-5 by the restriction enzyme BglI.

FIG. 5 shows the detection of amplified mycobacterial DNA sequences by the oligonucleotide restriction test.

The purified mycobacterial DNA is amplified, and equivalent amounts of the amplified product from *M. avium* (column 1–5), *M. bovis* BCG (column 6) and *M. fortuitum* (column 7) are evaluated as described above, using the oligonucleotide TB-5 labelled with $^{32}$P and the restriction enzyme BglI. An amount of enzyme corresponding to the following enzymatic activities is added: 1 unit (samples 1, 6 and 7); 5 units (sample 2); 10 units (sample 3); 20 units (sample 4); and 50 units (sample 5).

The autoradiogram is exposed for 3 hours with a single intensification screen. FIG. 5 shows clearly that only columns 1–5 enable the cleaved oligomer to be demonstrated, hence permitting identification of *M. avium*.

Example 7

Detection of mycobacterial DNA in a sputum specimen.

DNA purified from *M. tuberculosis* (FIG. 6, T), from *M. avium* (FIG. 6, A) and from *M. fortuitum* (FIG. 6, F) and DNA extracted from sputum samples which yielded a negative culture (FIG. 6, columns 1–6) or from sputum samples which yielded a positive culture for *M. tuberculosis* (FIG. 6, columns 7 and 8) was amplified using Taq polymerase in the case of the PCR or using another polymerase and the oligonucleotides TB-1 (SEQ ID NO:9) and TB-2 (SEQ ID NO:10). Samples of the amplified sequences are bound to filters (dot blots) and hybridised with the oligonucleotides TB-4 (SEQ ID NO:12), TB-5 (SEQ ID NO:13) and TB-6 (SEQ ID NO:14) labelled at their 5' end with $^{32}$P.

It is seen that the DNA of *M. tuberculosis* hybridises with TB-4 (SEQ ID NO:12).

As is apparent from the foregoing, the invention is in no way limited to those of its methods of implementation, embodiments and methods of use which have just been described more explicitly; on the contrary, it encompasses all variants which may occur to the specialist in the field without departing from the scope or range of the present invention.

5,817,459

We claim:

1. Nucleotide sequence derived from Actinomycetales, having respectively at its 5' and 3' ends, a sequence of formula (IX) (SEQ ID No:9):

5'GAGATCGAGCTGGAGGATCC (TB-1) and a sequence complementary to formula (X) (SEQ ID NO:10): 5'AGCTGCAGCCCAAAGGTGTT (TB-2) and in between a nucleotide fragment of 343 nucleotides of the gene that encodes a 65-kD mycobacterial antigen of Actinomycetales selected from the group consisting of mycobacteria, Nocardia and Rhodococcus.

2. An oligonucleotide having the sequence of formula (IX) (SEQ ID NO:9):

5'GAGATCGAGCTGGAGGATCC    (IX)

or exact complement thereof.

3. An oligonucleotide having the sequence of formula (IX) (SEQ ID NO:9):

5'AGCTGCAGCCCAAAGGTGTT    (IX)

or exact complement thereof.

4. An oligonucleotide having the sequence of formula (XI) (SEQ ID NO:11):

5'GCGGCATCGAAAAGGCCGTG    (XI)

or exact complement thereof.

5. An oligonucleotide having the sequence of formula (XII) (SEQ ID NO:12):

5'CGAAATCGCTGCGGTGGCCG    (XII)

or exact complement thereof.

6. An oligonucleotide having the sequence of formula (XIII) (SEQ ID NO:13):

5'CTGCCACCGCGGCCATCTCC    (XIII)

or exact complement thereof.

7. Oligonucleotide according to claim 6, wherein it comprises a single BglI restriction site.

8. An oligonucleotide having the sequence of formula (XIV) (SEQ ID NO:14):

5'CTGCCACCGCCGGTATCTCC    (XIV)

or exact complement thereof.

9. An oligonucleotide having the sequence of formula (XV) (SEQ ID NO:15):

5'AACGTCGCGGCCGGCGCCAA 3'    (XV)

or exact complement thereof.

10. An oligonucleotide having the sequence of formula (XVI) (SEQ ID NO:16):

5'GACTCCTCGACGGTGATGAC 3'    (XVI)

or exact complement thereof.

11. An oligonucleotide having the sequence of formula (XVII) (SEQ ID NO:17):

5'CCTGCTCAAGGGCGCCAAG 3'    (XVII)

or exact complement thereof.

12. Oligonucleotide according to claim 11, wherein it comprises a single BanI restriction site.

13. An oligonucleotide having the sequence of formula (XVIII) (SEQ ID NO:18):

5'CGAAATCGCTGCGGTGGCCGCAATCTGCTC 3'    (XVIII)

or exact complement thereof.

14. An oligonucleotide having the sequence of formula (XIX) (SEQ ID NO:19):

5'GGTGCTCGCCCAGGCGTTGGTCCGC 3'    (XIX)

or exact complement thereof.

15. An oligonucleotide having the sequence of formula (XX) (SEQ ID NO:20):

5'TGTGCTCGCCGCAGGCGCTGGTCAAA 3'    (XIX)

or exact complement thereof.

16. Pairs of primers for the synthesis of an Actinomycetales DNA or RNA of 343 bp, wherein they are selected from the group consisting of:
an oligonucleotide of formula (IX) (SEQ ID NO:9) (TB-1) paired with an oligonucleotide of formula (X) (SEQ ID NO:10) (TB-2);
an oligonucleotide of formula (XV) (SEQ ID NO:15) (TB-7) paired with an oligonucleotide of formula (XVI) (SEQ ID NO:16) (TB-8).

17. A labeled nucleotide probe wherein it is chosen from the group consisting of the oligonucleotides of formulae XI (SEQ ID NO:11) TB-3), XII (SEQ ID NO:12) (TB-4), XIII (SEQ ID NO:13) (TB-5), XIV (SEQ ID NO:14) (TB-6), XVII (SEQ ID NO:17) (TB-9), XVIII (SEQ ID NO:18) (TB-10), XIX (SEQ ID NO:19) (TB-1 1) and XX (SEQ ID NO:20) (TB-12).

18. A method for the detection and rapid identification, by amplification and hybridization, of small amounts of Actinomycetales selected from the group consisting of mycobacteria, Nocardia and Rhodococcus, possibly present in a biological sample suitably treated to extract the DNA and/or the transcription products of the said Actinomycetales, which method is characterized in that the said sample:
(1) is brought into contact with a pair of primers selected from the group consisting of an oligonucleotide of formula (IX) (SEQ ID NO:9) (TB-1) paired with an oligonucleotide of formula (X) (SEQ ID NO:10) (TB-2) and an oligonucleotide of formula (XV) (SEQ ID NO:15) (TB-7) paired with an oligonucleotide of formula (XVI) (SEQ ID NO:16) (TB-8),
to amplify at least one fragment of the said DNA or RNA, and
(2) detecting said at least one fragment with at least one labeled nucleotide probe comprising an oligonucleotide selected from the group consisting of formula II (SEQ ID NO:2), formula III (SEQ ID NO:3), formula IV (SEQ ID NO:4), formula V (SEQ ID NO:5), formula VI (SEQ ID NO:6), formula VII (SEQ ID NO:7), formula VIII (SEQ ID NO:8), formula IX (SEQ ID NO:9), formula X (SEQ ID NO:10), formula XI (SEQ ID NO:11), formula XII (SEQ ID NO:12), formula XIII (SEQ ID NO:13), formula XIV (SEQ ID NO:14), formula XV (SEQ ID NO:15), formula XVI (SEQ ID NO:16), formula XVII (SEQ ID NO:17), formula XVIII (SEQ ID NO:18), formula XIX (SEQ ID NO:19), and formula XX (SEQ ID NO:20).

19. Process according to claim 18, characterised in that it comprises in addition:
(3) cleavage of any probe which has hybridised during the above step (2), using a suitable restriction enzyme.

20. A method according to claim 19 wherein the restriction enzyme is selected from the group consisting of BanI and BglI.

21. Method according to claim 18, wherein the detection of the amplified DNA or RNA sequence is carried out using two suitable nucleotide probes, said method comprising in addition: p1 (3) enzymatic coupling of the two hybridised probes; p1 (4) detection of any fragment obtained containing the two combined probes.

22. Method according to any one of claims 18 to 21 wherein the DNA is isolated from the biological sample during a step prior to the detection and identification steps, by suspending the centrifugation pellet from the said biological sample in a suitable lysis solution, followed by an incubation at approximately 95° C. for a suitable time, the incubation itself being followed by the addition of a buffer solution to the medium, after which the DNA is extracted by suitable means of extraction.

23. Method according to claim 22, wherein the lysis solution employed is a solution comprising 0.1N NaOH, 2M NaCl and 0.5% SDS.

24. Method according to claim 22, wherein the incubation is carried out at a temperature of approximately 95° C. for approximately 15 minutes.

25. Method according to claim 23 wherein the incubation is carried out at a temperature of approximately 95 °C. for approximately 15 minutes.

26. A ready-to-use kit, outfit or coordinated set for carrying out a method for the detection and rapid identification by amplification and hybridization of small amounts of Actinomycetales selected from the group consisting of mycobacteria, Nocardia and Rhodococcus, possibly present in a biological sample, characterized in that it comprises appropriate amounts of suitable buffers and reagents for carrying out the said detection; suitable doses of a pair of primers selected from the group consisting of an oligonucleotide of formula (IX) (SEQ ID NO:9) (TB-1) paired with an oligonucleotide of formula (X) (SEQ ID NO:10) (TB-2), and an oligonucleotide of formula (XV) (SEQ ID NO:15) (TB-7) paired with an oligonucleotide of formula (XVI) (SEQ ID NO:16) (TB-8); and suitable doses of at least one nucleotide probe comprising an oligonucleotide selected from the group consisting of formula II (SEQ ID NO:2), formula III (SEQ ID NO:3), formula IV (SEQ ID NO:4), formula V (SEQ ID NO:5), formula VI (SEQ ID NO:6), formula VII (SEQ ID NO:7), formula VIII (SEQ ID NO:8), formula IX (SEQ ID NO:9), formula X (SEQ ID NO:10), formula XI (SEQ ID NO:11), formula XII (SEQ ID NO:12), formula III (SEQ ID NO:13),formula XIV (SEQ ID NO:14), formula XV (SEQ ID NO:15), formula XVI (SEQ ID NO:16), formula XVII (SEQ ID NO:17), formula XVIII (SEQ ID NO:18), formula XIX (SEQ ID NO:19), and formula XX (SEQ ID NO:20).

27. A nucleotide sequence derived from Actinomycetales, comprising a sequence of 383 nucleotides having respectively at its 5' and 3' ends, a sequence of formula (IX) (SEQ ID No:9): 5'GAGATCGAGCTGGAGGATCC (TB-1) and a sequence complementary to formula (X) (SEQ ID NO:10):
5'AGCTGCAGCCCAAAGGTGTT (TB-2), and in between a nucleotide fragment of 343 nucleotides of the gene that encodes a 65-kD mycobacterial antigen of Actinomycetales selected from the group consisting of mycobacteria, Nocardia and Rhodococcus.

28. Sequence according to claim 1, wherein said nucleotide fragment has the sequence of formula (II) (SEQ ID NO:2).

29. Sequence according to claim 1 wherein said nucleotide fragment has the sequence of formula (III) (SEQ ID NO:3).

30. Sequence according to claim 1 wherein said nucleotide fragment has the sequence of formula (IV) (SEQ ID NO:4).

31. Sequence according to claim 1 wherein said nucleotide fragment has the sequence of formula (V) (SEQ ID NO:5).

32. Sequence according to claim 1 wherein said nucleotide fragment has the sequence of formula (VI) (SEQ ID NO:6).

33. Sequence according to claim 1 wherein said nucleotide fragment has the sequence of formula (VII) (SEQ ID NO:7).

34. Sequence according to claim 1 wherein said nucleotide fragment has the sequence of formula (VIII) (SEQ ID NO:8).

35. The complement of the nucleotide sequence of claim 1.

36. The complement of the nucleotide sequence of claim 27.

37. Sequence according to claim 27, wherein said nucleotide fragment has the sequence of formula (II) (SEQ ID NO: 2).

38. Sequence according to claim 27, wherein said nucleotide fragment has the sequence of formula (III) (SEQ ID NO: 3).

39. Sequence according to claim 27, wherein said nucleotide fragment has the sequence of formula (IV) (SEQ ID NO: 4).

40. Sequence according to claim 27, wherein said nucleotide fragment has the sequence of formula (V) (SEQ ID NO: 5).

41. Sequence according to claim 27, wherein said nucleotide fragment has the sequence of formula (VI) (SEQ ID NO: 6).

42. Sequence according to claim 27, wherein said nucleotide fragment has the sequence of formula (VII) (SEQ ID NO: 7).

43. Sequence according to claim 27, wherein said nucleotide fragment has the sequence of formula (VIII) (SEQ ID NO: 8).

44. Sequence according to claim 28, wherein it comprises the following restriction sites:

AccII, AhaII, BanI, BanII, BbvI, Bsp1286, BstXI, CfoI, DdeI, EcoRII, EspI, Fnu4HI, HaeII, HaeII, HapII, HgaI, HinfI, HphI, MaeIII, MboII, MnlI, NarI, NcoI, NlaIII, SacI, SacII, Sau3A, Sau96A, ScrFI, StyI, TaqI, YmaIII.

45. Sequence according to claim 29, wherein it comprises the following restriction sites:

AccII, AflI, AhaII, BanI, BbvI, BglI, Bsp1286, BstEII, BstXI, CfoI, EaeI, HaeII, HaeII, HphI, MaeIII, MnlI, NarI, PvuI, SacII, Sau3A, Sau96A, TaqI.

46. Sequence according to claim 30, wherein it comprises the following restriction sites:

AccII, AhaII, BanI, BbvI, BstXI, CfoI, EaeI, HaeIII, HphI, MaeIII, MnlI, NarI, NrvI, SacII, Sau3A, Sau96A, TaqI.

47. Sequence according to claim 31, wherein it comprises the following restriction sites:

AccII, AhaII, AluI, AosI, BanI, BglI, Bsp1286, BstEII, CfoI, EaeI, HapII, HgaI, HphI, MboII, MnlI, NaeI, NlaIII, RsaI, Sau3A, Sau96A, SfaNI, StyI, TaqI, Tth111I.

48. Sequence according to claim 32, wherein it comprises the following restriction sites:

AccII, AhaII, AluI, AosI, BanI, BstEII, EaeI, EspI, Fnu4HI, HaeII, HinfI, HphI, MboII, MnlI, NaeI, Sau3A, StyI, TaqI.

49. Sequence according to claim 33, wherein it comprises the following restriction sites:

AatI, AosI, AhaII, AluI, BbvI, BstEII, CfoI, EaeI, Fnu4HI, HaeII, HapII, HinfI, MboII, MnlI, NaeI, PvuI, Sau3A, SytI, TaqI, Tth111I.

50. Sequence according to claim 34, wherein it comprises, the following restriction sites:

AccII, AhaII, AluI, AosI, BanI, Bsp1286, CfoI, EaeI, Fnu4HI, HaeIII, HgaI, HphI, MaeIII, MboII, MnlI, NlaIII, SacII, Sau3A, Sau96A, SfaNI, StyI, TaqI, Tth111I.

51. A labeled nucleotide probe having a nucleotide sequence according to any one of claims 1–15, and 37–43.

52. Sequence according to claim 27, that encodes the expression product having an amino acid sequence of the following formula (I) (SEQ ID NO:1):

$X_1$ — TYR — GLU — LYS — ILE — GLY — ALA — GLU — LEU — VAL — $X_2$ — GLU — VAL — ALA — LYS — LYS — THR — ASP — ASP — VAL — ALA — $X_3$ — ASP — $X_4$ — THR — THR — THR — ALA — THR — VAL — LEU — $X_5$ — GLN — $X_6$ — LEU — VAL — $X_7$ — GLU — GLY — LEU — ARG — ASN — VAL — ALA — ALA — GLY — ALA — ASN — $X_8$ — LEU — $X_9$ — $X_{10}$ — LYS — $X_{11}$ — GLY — ILE — GLU — LYS — ALA — VAL — GLU — $X_{12}$ — VAL — THR — $X_{13}$ — $X_{14}$ — LEU — LEU — $X_{15}$ — $X_{16}$ — ALA — LYS — GLU — VAL — GLU — THR — LYS — $X_{17}$ — GLN — ILE — ALA — ALA — THR — ALA — $X_{18}$ — ILE — SER — $X_{19}$ — GLY — ASP — $X_{20}$ — SER — ILE — GLY — $X_{21}$ — $X_{22}$ — ILE — $X_{23}$ — $X_{24}$ — $X_{25}$ — MET — ASP — LYS — VAL — GLY — $X_{26}$ — GLU — GLY — VAL — ILE — THR — $X_{27}$ — $X_{28}$ — GLU — SER — $X_{29}$ $X_1$-TYR-GLU-LYS-ILE-GLY-ALA-GLU-LEU-VAL-$X_2$-GLU-VAL-ALA-LYS-LYS-THR-ASP-ASP-VAL-ALA-$X_3$-ASP-$X_4$-THR-THR-THR-ALA-THR-VAL-LEU-$X_5$-GLN-$X_6$-LEU-AL-$X_7$-GLU-GLY-LEU-ARG-ASN-VAL-ALA-ALA-GLY-ALA-ASN-$X_8$-LEU-$X_9$-$X_{10}$-LYS-$X_{11}$-GLY-ILE-GLU-LYS-ALA-VAL-GLU-$X_{12}$-VAL-THR-$X_{13}$-$X_{14}$-LEU-LEU-$X_{15}$-$X_{16}$-ALA-LYS-GLU-VAL-GLU-THR-LYS-$X_{17}$-GLN-ILE-ALA-ALA-THR-ALA-$X_{18}$-ILE-SER-$X_{19}$-GLY-ASP-$X_{20}$-SER-ILE-GLY-$X_{21}$-$X_{22}$-ILE-$X_{23}$-$X_{24}$-$X_{25}$-MET-ASP-LYS-VAL-GLY-$X_{26}$ GLU-GLY-VAL-ILE-THR-$X_{27}$-$X_{28}$-GLU-SER-$X_{29}$ in which:

$X_1$ is void or represents the sequence ASP-PRO,
$X_2$ represents LYS or GLU,
$X_3$ represents GLY or ALA,
$X_4$ represents GLY or ARG,
$X_5$ represents ALA or VAL,
$X_6$ represents ALA or ARG,
$X_7$ represents ARG or LYS,
$X_8$ represents PRO or LEU,
$X_9$ represents GLY or SER,
$X_{10}$ represents LEU or PHE,
$X_{11}$ represents ARG or CYS,
$X_{12}$ represents LYS or ALA,
$X_{13}$ represents GLU or ALA,
$X_{14}$ represents THR or LYS,
$X_{15}$ represents LYS or ASP,
$X_{16}$ represents SER, GLY, PRO or THR,
$X_{17}$ represents ASP or GLU,
$X_{18}$ represents ALA, GLY or VAL,
$X_{19}$ represents ALA or VAL,
$X_{20}$ represents GLN or ALA,
$X_{21}$ represents ASP or GLU,
$X_{22}$ represents LEU or PRO,
$X_{23}$ represents ALA or VAL,
$X_{24}$ represents GLU or ASP,
$X_{25}$ represents ALA or GLY,
$X_{26}$ represents ASN or LYS,
$X_{27}$ represents VAL or SER,
$X_{28}$ represents GLU or GLY, $X_{29}$ is void or represents the sequence ASN-THR-PHE-GLY-LEU-GLN.

* * * * *